US009016522B2

(12) United States Patent
Hayman et al.

(10) Patent No.: US 9,016,522 B2
(45) Date of Patent: Apr. 28, 2015

(54) MULTI-COMPARTMENT DEVICES HAVING DISPENSING TIPS

(75) Inventors: Robert Hayman, Los Angeles, CA (US); Eric P. Rose, Tarzana, CA (US); William Landsman, Porter Ranch, CA (US); John Raybuck, Los Angeles, CA (US); Marc Orloff, Glendale, CA (US)

(73) Assignee: Discus Dental, LLC, Culver City, CA (US)

( * ) Notice: Subject to any disclaimer, the term of this patent is extended or adjusted under 35 U.S.C. 154(b) by 1489 days.

(21) Appl. No.: 12/335,288

(22) Filed: Dec. 15, 2008

(65) Prior Publication Data

US 2009/0152300 A1 Jun. 18, 2009

Related U.S. Application Data

(60) Provisional application No. 61/013,996, filed on Dec. 14, 2007.

(51) Int. Cl.

| | |
|---|---|
| ***B67D 7/70*** | (2010.01) |
| ***B67D 7/78*** | (2010.01) |
| ***B65D 47/10*** | (2006.01) |
| ***B01F 5/06*** | (2006.01) |
| ***A61C 5/06*** | (2006.01) |
| ***B01F 13/00*** | (2006.01) |
| ***B01F 15/00*** | (2006.01) |

(52) U.S. Cl.

CPC ............... *B01F 5/0615* (2013.01); *A61C 5/062* (2013.01); *A61C 5/064* (2013.01); *B01F 13/002* (2013.01); *B01F 13/0022* (2013.01); *B01F 15/0087* (2013.01); *B01F 2005/0637* (2013.01)

(58) Field of Classification Search

USPC ........ 222/137, 145.6, 145.1, 386, 386.5, 459, 222/153.09, 145.5, 135, 541.5, 541.6, 222/541.8; 239/399

See application file for complete search history.

(56) References Cited

U.S. PATENT DOCUMENTS

| | | | | |
|---|---|---|---|---|
| 4,776,704 | A * | 10/1988 | Kopunek et al. | 366/184 |
| 5,819,988 | A | 10/1998 | Sawhney | |
| 6,065,645 | A | 5/2000 | Sawhney | |
| 6,322,773 | B1 | 11/2001 | Montgomery | |
| 6,394,314 | B1 | 5/2002 | Sawhney | |
| 6,536,628 | B2 | 3/2003 | Montgomery | |
| 6,564,972 | B2 | 5/2003 | Sawhney | |
| 6,691,932 | B1 * | 2/2004 | Schultz et al. | 239/401 |
| 6,698,622 | B2 | 3/2004 | Sawhney | |
| 2001/0004082 | A1 * | 6/2001 | Keller et al. | 222/137 |
| 2006/0198794 | A1 | 9/2006 | Montgomery | |
| 2008/0131380 | A1 | 6/2008 | Montgomery | |

FOREIGN PATENT DOCUMENTS

| | | |
|---|---|---|
| WO | 00/21842 | 4/2000 |

* cited by examiner

*Primary Examiner* — Kevin P Shaver
*Assistant Examiner* — Stephanie E Williams

(57) ABSTRACT

The present invention relates to multi-compartment devices having a pre-applied dispensing element. The device is adapted for dispensing multi-component compositions that are kept separate prior to use. Supplying a pre-applied dispensing element facilitates and simplifies the dispensing operation during use and reduces the chance of misuse due to improper application of the mixing element, loss and/or damage of the component.

19 Claims, 31 Drawing Sheets

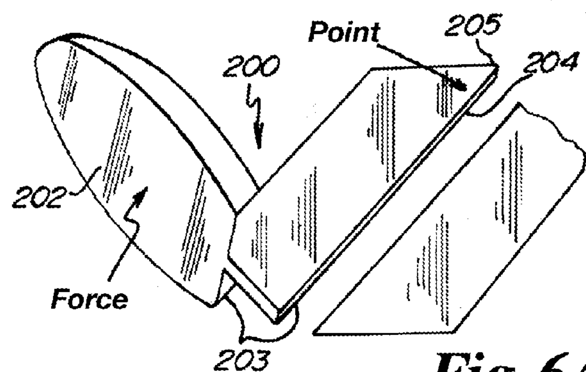
Fig. 6A.
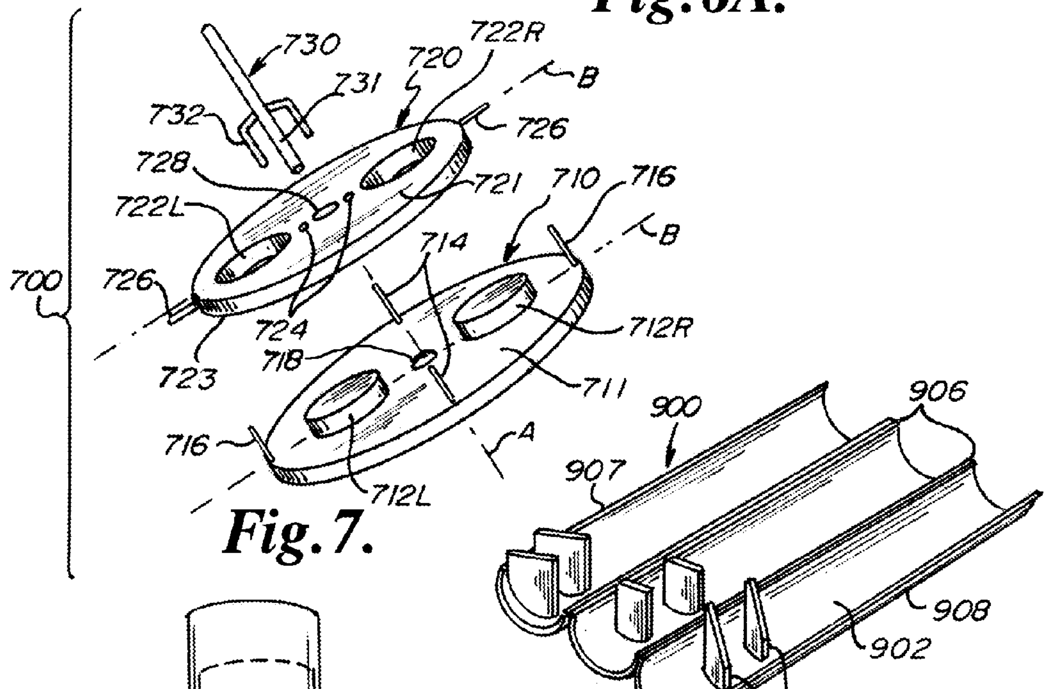
Fig. 7.
Fig. 9.
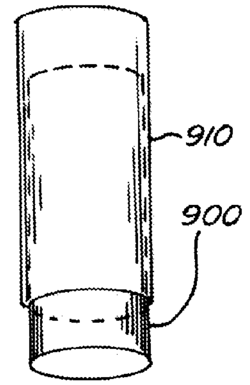
Fig. 9B.

MULTI-COMPARTMENT DEVICES HAVING DISPENSING TIPS

FIELD OF THE INVENTION

The present invention is related to multi-compartment devices for storing, and dispensing viscous substances. In particular, the invention relates to a multi-compartment device having dispensing tips for dispensing an admixture.

BACKGROUND

Dental practitioners utilize syringes for a variety of tasks and procedures, including storing and dispensing substances used in dental procedures. Many compositions have a single component, but many others are composed of multiple components that are kept separate before a procedure, including, but not limited to, whitening compositions, impression materials, dentifrices and the like.

Multi-barreled or multi-compartment devices are often utilized to store the multiple components of a composition and may also be used to mix and dispense the composition for use. As it is typically desired to keep the components separate to prevent any premature interaction, it is important for a device to incorporate features that maintain the integrity of the composition during storage.

SUMMARY OF THE INVENTION

The present invention relates to multi-compartment devices having a pre-applied dispensing element. The device is adapted for dispensing multi-component compositions that are kept separate prior to use. Supplying a pre-applied dispensing element facilitates and simplifies the dispensing operation during use and reduces the chance of misuse due to improper application of the mixing element, loss and/or damage of the component.

Many multi-component compositions are also typically mixed prior to use to properly combine the constituents in order to form an active and/or working composition. In one embodiment, a pre-applied dispensing element includes a mixing element, for dispensing and/or mixing the compositions. Supplying a pre-applied dispensing and/or mixing element facilitates and simplifies the dispensing operation during use and reduces the chance of misuse due to improper application of the mixing element, loss and/or damage of the component.

In one aspect, the tip may serve as a dispensing means. In another aspect, the tip may serve both as a dispensing and a mixing means.

The present invention relates to a multi-chambered device for storing and dispensing the material components of an admixture, including a housing having at least two chambers, each of said chambers having an outlet and an inlet with full fluid communication between the inlet and the outlet. A dispensing and/or mixing tip may be attached to the housing about the outlets of the chambers. The tip may have a generally axial bore, an inlet and an outlet. The device may include a unitary construction multi-plunger having juxtaposed plungers integrally molded from a polymeric material.

In one aspect, multi-compartment devices may in general be in the form of a multi-barreled syringe, in particular double-barreled assemblies. The double-barreled syringes may include double-plungers. In another aspect, other numbers of barrels are also conceived and contemplated.

The multi-compartment devices include sealing systems for keeping the components separate. In one embodiment, a multi-compartment device incorporates features, for example, formations, that may be adapted to allow the components of a composition to remain substantially segregated and sealed off until use. Such features may be adapted to cooperate with corresponding features on the rest of the device.

At least one sealing system may be configured for substantially sealing the outlets of the chambers during storage, and at least one formation maybe configured for effecting the unsealing of the outlets of the chambers. In one example, at least a portion of the sealing system may be disposed within the bore of the tip. For example, the at least one seal breaking components may be configured to puncture or remove the seal when applying pressure to the contents of the chambers from the inlet ends.

In one exemplary embodiment, such features, once activated to allow the contents of a compartment to exit the compartment, may be irreversible. In one aspect, the vessel, compartments may include an inert and/or unreactive substance that may act as a plug and/or sealant that may be forced out to allow mixing of the components of a composition.

In one embodiment, the tip may include at least one cap and at least one plug shape element adapted to be disposed inside the at least one cap. A mixing element is attached and integral with the plug shape element, and maybe adapted for introducing the plug shape element into the barrel region of the syringe body. The pockets or hollow interiors of the barrel or barrels may have a corresponding feature for receiving the plug shape element so that the exit openings of the barrel or barrels may be closed by the plug shape element. The cap of the tip may also include threads adapted for attaching to the barrel or barrels by screwing onto the base of the barrel or barrels and a ledge for pushing the plug element on the mixing element onto the pocket or pockets of the barrel or barrels, closing the openings.

In one embodiment, the at least one cap plug reversibly plugs the outlet of a chamber.

In another embodiment, the at least one cap plug irreversibly unplugs the outlet of a chamber when removed.

In another embodiment, the tip may include a mixing element adapted to be disposed inside the tip and a separate plug element adapted for fitting into the exit opening end of the barrel or barrels. The plug element may be forced into place on the barrel or barrels by attachment of the tip.

In another aspect, the features may include seals that may be forced and/or broken so as to allow the contents of a compartment to exit.

In one embodiment, a seal, such as a foil seal, may be introduced at the top of the barrel or barrels to seal off the content or contents. A formation, for example, a pointed formation, is adapted for breaking the seal may be introduced to the barrel or barrels before the barrel or barrels are filled with compositions. During use, the user may push on the plunger or plungers, driving the formation through the foil to open the barrel or barrels.

In another embodiment, a removable seal, which may be a foil seal, may be introduced at the top of the barrel or barrels to seal off the content or contents. The barrel or barrels may be modified to include a cap which may be attached to the barrel or barrels with a living hinge. The cap may include a mixing element and adapted for attaching onto the opening end of the barrel or barrels. When the seal is removed, the cap may be onto the barrel or barrels for use.

In another exemplary embodiment, the multi-compartment devices may include a switching assembly that may allow the multiple chambers to be opened and/or closed such that the separated components of a composition may be dispensed together and/or segregated, respectively, when desired. In one aspect, the switching assembly may incorporate a rotatable portion that may allow a user to control the open or closed state of the compartments. In another aspect, the switching assembly may incorporate a pull/push closable feature that may unplug/plug the outlets of the compartments.

In another alternative embodiment, the compartments may include spatially segregated outlet ports that may substantially decrease the interaction of the components of a composition until an adequate amount of the components is dispensed such that the spatial segregation may be overcome to affect interaction and/or mixing of the components.

In yet another embodiment, the tip may incorporate a means of closing and/or sealing the delivery outlet point such that a user may prevent substantially all of the composition from exiting the mixing tip, when, for example, in a pause during a procedure or using said composition for multiple procedures.

In another exemplary embodiment, the multi-compartment device may include a double-barrel syringe body, a rotatable head, a mixing element, and a pre-mixing neck portion including two connecting channels. Each connecting channel extends from the outlet of each barrel and ends at a sealing surface located at the lower inner surface of the rotatable head. When the syringe is in a closed position, the sealing surface entirely blocks the discharge end of the connecting channel to prevent premature interaction between the components from the syringe barrels. In an open position, the sealing surface rotates away by slightly turning the rotatable head to enable the component from each barrel to move upwardly toward the mixing element.

In other embodiments, the multi-compartment device may include a double-barrel syringe body, a mixing tip, a mixing and switching assembly including a mixing element integrated with a plug, and a pre-mixing neck portion including two connecting channels with tapered ends. The plug includes at least two tapered units which tightly fit with the tapered ends of the connecting channels to form a tight seal to prevent the component in each barrel from premature mixing with each other. The mixing tip may include a tip portion and a threaded portion, the former closely receives the mixing and switching assembly, and the later is adapted to attach to the pre-mixing neck portion by screwing onto the outer surface thereof, wherein at least portion of the threaded portion of the mixing tip engages with at least portion of the plug which is forced down to close the outlet of the barrel. An opened position may be achieved when a user makes an upward quarter or half turn of the mixing tip to disengage the plug, and when appropriate external force is applied to the components in the barrels, the disengaged mixing and switching assembly is accordingly lifted away from the closed position to allow the component in each barrel to move toward the tip portion of the mixing tip where the components can be mixed in the manner as stated previously. The device can be resealed simply by screwing down the mixing tip again. In another aspect, the mixing element is not integrated with the plug.

In still another aspect, the tip itself may serve as a plug. For example, a hemispheric channel blocker is located within the mixing tip, wherein the outer surface of the hemispheric channel blocker is adapted to block each connecting channel. When the mixing tip is screwed all the way down to close the syringe, the outer surface of the hemispheric channel blocker substantially blocks each connecting channel to prevent the components in the barrels from leaking or premature mixing with the other component. The syringe can be opened when a user makes an upward quarter or half turn of the mixing tip to move the outer surface of the channel blocker away from the connecting channels, such that when appropriate force is applied from the double-plunger assembly to the components in the barrels, the component in each barrel is allowed to move toward the tip portion of the mixing tip where the components are mixed to form an admixture for dispensing. The syringe in the present embodiment can be resealed simply by screwing down the mixing tip again.

In one embodiment of the invention, the multi-compartment device may include a syringe body, which may include a double-barrel assembly having juxtaposed first and second barrels having a common length and a generally cylindrical bore. Each barrel is bounded at a discharge end by first and second shoulders, respectively, with each shoulder having a generally planar surface. The surfaces are coplanar and contiguous. A generally cylindrical neck extends from and is substantially symmetrically disposed between the shoulders. The neck includes first and second outlet passages. Each barrel at its opposite (plunger) end closely receives a piston within its bore. An arcuately-shaped finger-grip circumscribes the contiguous plunger ends of the barrels. The syringe body further includes a double-plunger assembly having juxtaposed first and second plungers of a common length. Each plunger extends at a proximal end in an end-piece rigidly attached to one of the pistons, and is rigidly attached at a distal end to a thumb-rest common to the plungers.

In one embodiment, the diameters or sizes of the barrels or compartments may be the same, for example, in a 1:1 ratio. In another embodiment, the diameters or sizes of the barrels or compartments may be different, for example, in a ratio of 1:2 to 1:5.

In one aspect, the syringe includes a pre-applied dispensing and/or mixing tip that may be integrally or detachably attached to the syringe body. The dispensing and/or mixing tip may be generally conical in shape and may have an inlet end (Proximal), a discharge end (Distal) and a bore therethrough. The bore may be generally cylindrical at the inlet end and may extend in a conically tapered fashion toward the discharge end (Distal). The cylindrical bore portion may be determined by a circumferential surface that may be adapted to closely receive the body neck.

For a mixing tip, a static mixing element may be closely received and wedged within the bore of the tapered portion of the tip. The mixing tip may include at the inlet end a second mating assembly having opposed generally planar, arcuate first and second locking tabs of a common predetermined thickness slightly less than the distance between the rib locking faces of the first mating assembly and the neighboring shoulder. Each tab may have at least one edge beveled at a common predetermined angle. The tabs may be symmetrically disposed with respect to the cylindrical bore portion. The bore circumferential surface may include diametrically opposed first and second detent recesses and first and second ramps which may be contiguous at a proximal end, respectively, to the recesses.

In one embodiment, the static mixer may have a four section mixing element. Alternatively, a five section static mixing element may be received and wedged within the bore tapered portion. It has been observed that the use of a five section static mixing element may provide up to approximately 50% better mixing than the four section static mixing element. Those skilled in the art will appreciate that additional sections of the static mixing element may provide further enhanced mixing and may therefore be desirable.

In one aspect, each section of the static mixing element may include a single turn screw, intertwined blades, baffles and/or fins. Each screw may be clocked, i.e., configured so as to be right or left handed, opposite that of each adjacent screw and may be oriented, with respect to the leading and trailing edges thereof, at 90° with respect to each adjacent screw. Thus, as the two viscous materials flow from one screw to the next screw, the viscous materials may be split into two portions, such that it may effect the desired mixing thereof. The screws may be disposed upon a common shaft. The screws may taper in size such that the viscous materials may flow through successively smaller screws as the viscous materials are dispensed.

In one aspect, the screws may be disposed upon a common shaft. In another aspect, the screws may include at least one tapered section such that the materials may flow through the at least one tapered section as the materials are dispensed.

In some embodiments, the dispensing and/or mixing tip may be integrally formed onto the body of the syringe.

In other embodiments, the dispensing and/or mixing tip may be separate and/or detachable from the body of the syringe.

In an exemplary aspect, the mixing tip may be formed from a single molded piece. In one embodiment, the mixing tip piece may include multiple sections that may form, when viewed from its end, sectors of a full circle and may, when assembled properly, form a fully cylindrical, conical and/or other appropriately shaped tip that may have a substantially hollow interior. The interior surface of the mixing tip may also have a plurality of baffles, fins and/or other formations that may be adapted to facilitate the mixing tip's static mixing function when the tip is properly assembled. The baffles, fins and/or other formations may be formed onto the surfaces of the sections of the unassembled mixing tip during manufacture, such that the formations may be distributed in a desired fashion and/or pattern on the surfaces of the mixing tip sections.

In another aspect, the tip may include a dynamic mixing element. In one embodiment, the dynamic mixing element may include movable mixing formations to facilitate mixing of the components of a composition.

The present invention also relates to a multi-chambered device for storing and dispensing the material components of an admixture, including a housing having at least two chambers each having an outlet and an inlet with full fluid communication between the inlet and the outlet, and a dispensing tip adapted for attaching to the housing about the outlets of the chambers, said tip comprising an inlet, an outlet and a generally axial bore comprising a mixing and switching assembly disposed therein. The device may also include a pre-mixing neck portion having at least two connecting channels with full fluid communication between the housing and the dispensing tip when the device is in its open position. In one embodiment, each connecting channel is extended from the outlet of each chamber to a discharge end of the pre-mixing neck portion.

In one embodiment, the mixing and switching assembly may include a plug and a static or a dynamic mixing element for mixing at least two materials dispensed from the chambers.

In one aspect of any of the above embodiments, the plug may include at least two tapered units. According to one embodiment, the mixing element may be integrated with the plug. In another aspect, the tapered units of the plug substantially block the connecting channels. In a further aspect, at least a portion of the threads of the dispensing tip engage with the plug, such that when the tip may be screwed toward the closed position, the plug is forced down to close the discharge end of the pre-mixing neck portion. In yet another aspect, the dispensing tip may disengage with the plug when the tip is screwed toward the open position.

In another embodiment, the dispensing tip may include threads to rotatably control an open or closed position of the device.

In a further embodiment, the mixing element may be disposed separately with the plug and may include a disc and at least two legs extended therefrom.

In one aspect of any of the embodiments above, the legs of the plug may substantially block the connecting channels. In another aspect, the at least portion of the threads of the dispensing tip may engage with the disc of the plug, such that when the tip is screwed toward the closed position, the plug is forced down to close the discharge end of the pre-mixing neck portion. At the same time, the dispensing tip may disengage with the disc when the tip is screwed toward the open position.

In still another embodiment, a mixing element may be disposed separately with the plug which is integrated with at least portion of the dispensing tip.

In one aspect of any of the embodiments above, the plug may be located within the dispensing tip. At least portion of the threads of the dispensing tip may engage with corresponding threads of the neck portion, such that when the tip is screwed toward the closed position, the plug is accordingly moved down toward the connecting channels. In another aspect, an outer surface of the plug may substantially block the connecting channels. The outer surface of the plug may be moved away when the tip is screwed toward the open position.

The present invention further relates to a dispensing and mixing tip. The tip has a body having multiple sections and two free edges, each of said multiple sections having an inner surface and an outer surface; and multiple formations extending from the inner surfaces of the multiple sections. The two free edges of the multiple sections may be joined to form a conduit and the multiple formations may be arranged to form a mixing system within the conduit of the tip. The multiple formations may be staggered, angled or aligned. The body may also be of unitary construction.

In one embodiment, the formations of the dispensing and mixing tip may include fins, blades, baffles or combinations thereof.

In another embodiment, the mixing system may include a static or a dynamic element.

In a further embodiment, the body may be adapted for rotation within an external housing.

Any of the above embodiments and aspects of the invention may be applicable to all other inventions, embodiments and aspects.

The present invention together with the above and other advantages may best be understood from the following detailed description of the embodiments of the invention illustrated in the drawings below.

BRIEF DESCRIPTION OF THE DRAWINGS

FIG. 6A is a perspective view of a seal breaker of FIG. 6;

FIG. 7 is an exploded perspective view of a double-barreled syringe manual control system;

FIG. 9 is a perspective view of a mixing and dispensing tip with integral static mixing formations;

FIG. 9B is a partial see-through perspective view of a mixing and dispensing tip within an external form;

DETAILED DESCRIPTION OF THE INVENTION

Figure 1:
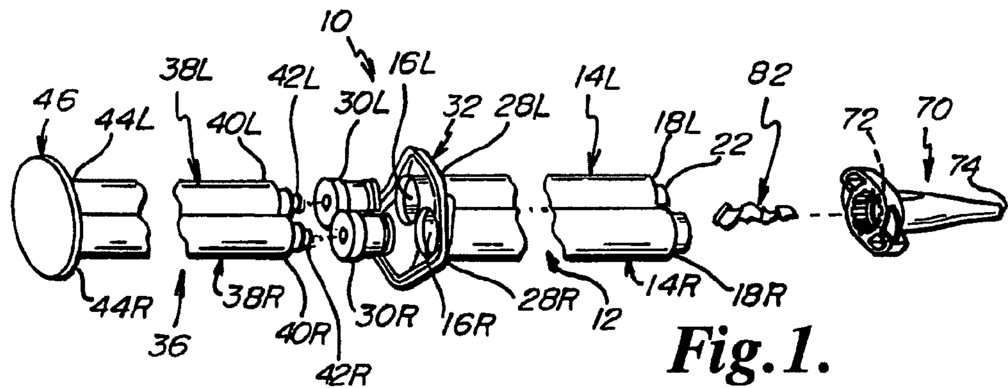
FIG. 1 is an exploded perspective view of a double-barreled syringe according to the invention, including a double-plunger assembly, two pistons, a double-barrel assembly, a static mixing element, and an applied dispensing and/or mixing tip.

While the present invention is open to various modifications and alternative constructions, the embodiments shown in the drawings will be described herein in detail. It is to be understood, however, there is no intention to limit the invention to the particular form disclosed. On the contrary, it is intended that the invention cover all modifications, equivalences and alternative constructions falling within the spirit and scope of the invention as expressed in the appended claims.

The invention relates to an article of manufacture which is primarily intended for storing and dispensing gels which are components of an admixture that may need to be kept separate until the admixture is formed. However, the invention is not limited to particular types of material to be stored and dispensed, and can be used for storing and dispensing any material that can be placed within a syringe barrel and effectively admixed by a static or dynamic mixing tip.

Where used herein, the word "attached" means that the two parts referred to (e.g., a locking rib and a shoulder or a plunger end-piece and a piston) are either molded in a single piece, are glued, slip onto one another, friction fit or force-fitted together, and may or may not be easily separated after being joined together. However, other forms of attachment may be suitable, consistent with simplicity of manufacture and reliability of operation. Where used herein, the word "connected" means that the two parts referred to (viz., the two mating assemblies) can be easily separated after being joined together in an interlocking combination.

Figure 2:
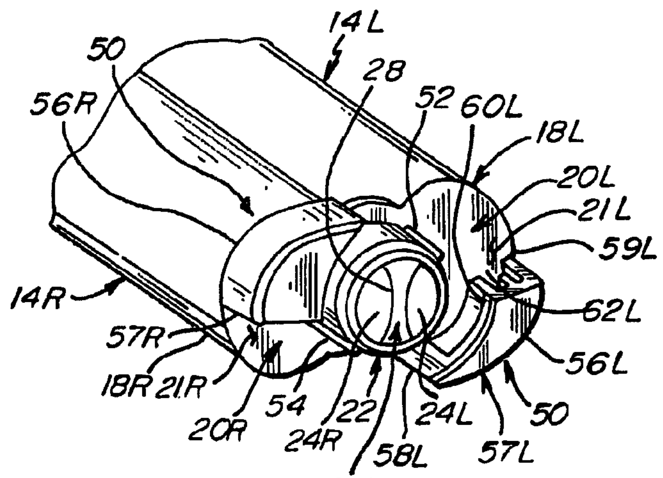
FIG. 2 is a discharge end perspective view of the FIG. 1 double-barrel assembly, including two shoulders, a neck with two outlet passages, and a mating assembly with two diametrically opposed detents and two symmetrically disposed locking ribs for engaging and interlocking with the dispensing and/or mixing tip.

Referring to FIGS. 1 and 2, a syringe body 10 may include a double-barrel assembly 12 that may have juxtaposed first and second generally cylindrical barrels 14L, 14R which may have a common length and a generally cylindrical bore 16L, 16R, respectively, that may be of a common diameter that may determine storage compartments 15L (not shown), 15R (not shown). Barrels 14L, 14R may be bounded at a first (discharge) end 18L, 18R, respectively, by first and second shoulders 20L, 20R, respectively. The shoulders may have generally planar surfaces 21L, 21R, respectively, which may be coplanar and contiguous. A generally cylindrical neck 22 may extend from and may be, for example, substantially symmetrically disposed between the shoulders. As shown in FIG. 2, neck 22 may include first and second outlet passages 24L, 24R, which may be divided by a partition 26. Barrels 14L, 14R may be open at an opposite (plunger) end 28L, 28R, respectively, which may closely receive pistons 30L, 30R, respectively. Barrel ends 28L, 28R may be circumscribed by and rigidly attached to an arcuately-shaped finger-grip 32.

The syringe body 10 may further include a double-plunger assembly 36 that may have juxtaposed generally cylindrical first and second plungers 38L, 38R of a common length. Each plunger may extend at an end 40L, 40R proximal to a piston in an end-piece 42L, 42R that may be rigidly attached to the piston 30L, 30R, respectively. The plungers may be attached at their distal end 44L, 44R to, for example, a disc-shaped thumb-rest 46 such that when the thumb-rest is depressed the plungers may move forward in tandem, and the attached pistons may move in tandem within the barrels. In other embodiments, the plungers may be separate.

Still referring to FIG. 2, syringe body 10 may further include a first mating assembly 50 that may have diametrically opposed first and second detents 52, 54 that may extend outwardly from neck 22, and opposed first and second locking ribs 56L, 56R that may be, for example, substantially symmetrically disposed with respect to neck 22. Ribs 56L, 56R may each have a first (stand-off) portion 57L, 57R, respectively, which may be generally parallel to the shoulders 20L, 20R, respectively, and generally orthogonal to a second (bracket) portion 58L, 58R (not shown), respectively, which may be rigidly attached, respectively, to shoulders 20L, 20R. Rib stand-off portions 57L, 57R may each have two generally planar locking faces 59L, 60L, and 59R (not shown), 60R (not shown), respectively, which may be, for example, generally parallel to and at a generally common distance from the neighboring shoulder surface 21L, 21R, respectively, thus determining substantially symmetrical recesses 62L, 62R (not shown), respectively.

In some embodiments, double-barrel assembly 12, including neck 22, and mating assembly 50 may be fabricated as a unit from a suitable material, such as, for example, polymeric materials that may be biodegradable, compostable, recyclable, non biodegradable or non-recyclable and may include polypropylene, polyethylene, polycarbonate, polystyrene, polyacrylic polymers, polylactic acid, and/or any other suitable material. The double-barrel assembly 12 may be manufactured by a variety of methods such as, for example, various molding methods that may include injection-molding. Some materials may be colored to protect the constituents from exposure to UV and or light exposure. Also in addition, those skilled in the art may fabricate the unit from a material that may protect the constituents from drying out and from degrading due to exposure to certain elements in the air.

Figure 3:
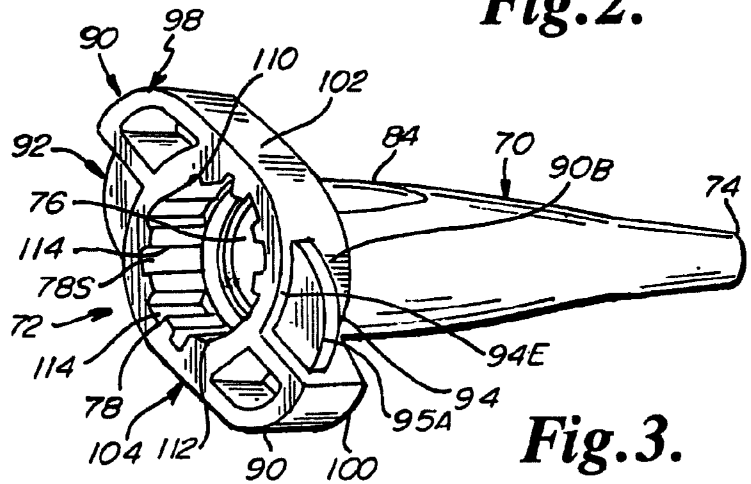
FIG. 3 is an inlet end perspective view of the FIG. 1 dispensing and/or mixing tip, including a mating assembly, having two locking tabs, which engages and interlocks with the FIG. 2 mating assembly.

Referring to FIGS. 1 and 3, the syringe body 10 may have disposed on it a pre-applied dispensing and/or mixing tip 70. The tip 70 may be attached to the syringe 10 at the time of manufacture and/or any time prior to the delivery to the customer. This may decrease the chance of loss and any subsequent loss of function and/or usability of components, decrease the complexity of usage and in general provide for an increase in convenience to the customer. The pre-applied tip 70 may be attached to the syringe 10' by permanent, integral and/or detachable means, and may include an inlet end 72 and a discharge end 74 and a bore 76 theretbrough. As best shown in FIG. 3, bore 76 may have a generally cylindrical portion 78 proximate to inlet end 72 and may extend in a conically tapered portion 80 (shown in FIG. 4B) toward the discharge end 74. Cylindrical bore portion 78 may be determined by a circumferential surface 78S that may be adapted to closely receive the neck 22.

Still referring to FIG. 3, the inlet end 72 of tip 70 may include a second mating assembly 90 that may have, for example, opposed generally planar and/or arcuately-shaped first and second locking tabs 92, 94 of a common predetermined thickness that may be slightly less than the common width of recesses 62L, 62R. Tabs 92, 94 may be, for example, substantially symmetrically disposed with respect to cylindrical bore portion 78 and may have edges 93A (not shown), 93B (not shown) and 95A, 95B, respectively, which may each be beveled at an angle of about 8 degrees. Tabs 92, 94 may be rigidly attached, respectively, to structural ribs 98, 100 which may be, for example, disposed substantially symmetrically with respect to bore portion 78, and may extend in generally oval-shaped collar portions 102, 104, respectively. The two collar portions may partially circumscribe inlet end 72 and extend such that tab 92 may be rigidly attached at an interior edge 92E (not shown) to collar portion 104, and tab 94 may be rigidly attached at an interior edge 94E to collar portion 102. Surface 78S may include substantially diametrically opposed first and second detent recesses 110, 112 and a plurality of corrugations 114.

In some embodiments, dispensing and/or mixing tip 70 and associated mating assembly 90 may be fabricated as a unit from a suitable material, including those suitable for the barrels or compartments mentioned above, for example. The tip 70 may be manufactured by a variety of methods such as, for example, various molding methods that may include injection-molding.

A mixing element, for example a static mixing element 82 may be closely received and wedged within the tapered bore portion 80. The static mixing element 82 may include a four section static mixing element in one embodiment. That is, the mixing element 82 may include four separate single turn screws. In another embodiment, the mixing element 82 may include a five section static mixing element. The mixing element 82 may be inserted in a random azimuthal orientation within bore portion 80 and so may not be disposed in a predetermined orientation with respect to partition 26 and outlet passages 24L, 24R when tip 70 is attached to double-barrel assembly 12.

Further examples of the mixing elements 82 may be found in U.S. Pat. Nos. 5,819,988, 6,065,645, 6,394,314, 6,564,972, 6,698,622, and 4,767,026, the contents of which are hereby incorporated by reference.

Figures 4, 4A, 4B, 4C:
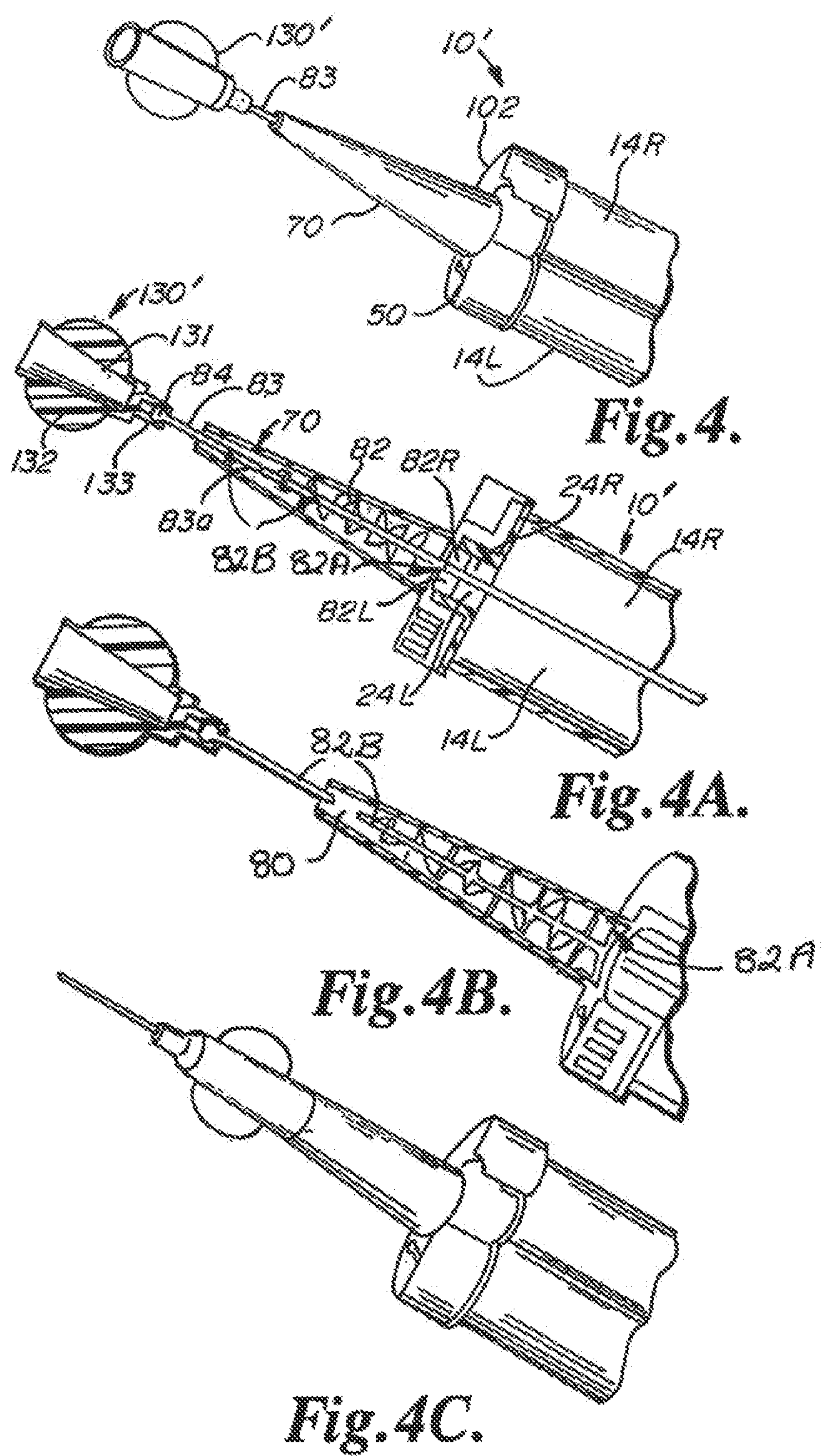
FIG. 4 is a partial perspective view of a double-barreled syringe with a pre-applied dispensing and mixing tip and a combined cap and pull tab in an exemplary embodiment of the invention.
FIG. 4A is a partial cross-sectional view of the double-barreled syringe assembly of FIG. 4.
FIG. 4B illustrates the usage of a break point with the double-barreled syringe assembly of FIG. 4.
FIG. 4C illustrates capping the double-barreled syringe assembly of FIG. 4.

FIG. 4 shows a partial perspective view of a double-barreled syringe 10' with a pre-applied dispensing and/or mixing tip 70 in an exemplary embodiment of the invention. The double-barreled syringe 10' may be substantially identical to the double-barreled syringe assembly 12 of FIG. 1.

In an exemplary embodiment, the syring 10' with pre-applied tip 70 may include integral or detachable means of isolating and/or sealing the contents of the syringe barrels 14R, 14L prior to use and may provide additional means of allowing interaction between the contents and/or closing the syringe. FIG. 4A shows a partial cross-sectional view of the syringe 10' with pre-applied dispensing and/or mixing tip 70 of FIG. 4. In one aspect, the pre-applied tip 70 may have disposed within a static mixing element 82 that may be substantially identical in form and function to the mixing element 82 as shown in FIG. 1. At least one sealing system 82A includes at least one cap plug 82R, 82L for substantially plugging the outlet of one of the chambers. In one embodiment, the static mixing element 82 may have the cap plugs 82R, 82L attached at the end proximal to the outlets 24R, 24l. The cap plugs 82R, 82L may substantially close and/or seal the outlets 24R, 24L, respectively and thus may substantially eliminate, minimize or prevent the release and/or interaction of the contents of the barrels 14R, 14L, respectively. Prior to use, the cap plugs 82R, 82L may be removed such that the contents of the barrels 14R, 14L may exit and may be dispensed and/or mixed. A seal breaking component 82B for effecting the unsealing of the outlets 24R, 24L includes a pull shaft 83, which may be attached to the static mixing element 82 at its end distal to the outlets 24R, 24L. The pull shaft 83 may extend beyond the end of the pre-applied tip 70 and may allow the user to effect the removal of the cap plugs 82R, 82L by means of pulling on the pull shaft 83 such that the static mixing element 82 and by virtue of its attachments, the cap plugs 82R, 82L may be shifted distally from the outlets 24R, 24L, thus opening them.

Since additional objects in the flow path of the pre-applied tip 70 may restrict the exiting of a composition therefrom, it may be desirable to remove pull shaft 83 after utilizing it to remove cap plugs 82R, 82L. A break point 83*a* may be included between the pull shaft 83 and the static mixing element 82 such that a properly applied and/or exerted force may effect its failure or breakage such that the pull shaft 83 may be removed from the flow path of the pre-applied tip 70 while retaining the static mixing element 82, if present, as shown in FIG. 4B. In general, the properly applied and/or exerted force necessary to effect failure or breakage at the break point 83*a* may be greater than the force required to remove the cap plugs 82R, 82L from the outlets 24R, 24L.

A mating formation 84 also may be included such that the pull shaft 83 may be attached to a handle and/or other component that may allow easier effecting of the pulling motion, such as the combined cap and pull tab 130' shown in FIGS. 4 and 4A. The combined cap and pull tab 130' may include a mating formation 133 that may substantially couple it to the mating formation 84 of the pull shaft 83. Thus, by pulling on the combined cap and pull tab 130', the user may effect the removal of the cap plugs 82R, 82L as discussed above with greater ease. The combined cap and pull tab 130' may also include features that may increase its grippability and/or its ease of handling, such as, for example, handle tabs 132, as shown in FIG. 4A. Other features, that may include, but are not limited to, textured gripping surfaces, pull bars that the users may hook their fingers around for better grip, and/or any other suitable features may be included. In general, the mating formations 84, 133 may maintain their interface up to and beyond the force required to remove the cap plugs 82R, 82L from outlets 24R, 24L as well as the force required to effect failure or breakage of breaking point 83*a*.

In an exemplary embodiment, the combined cap and pulling tab 130' may also include a feature, for example, a formation that may allow it to substantially cap and/or close the pre-applied tip 70. A hollow space 131 may be included, which may be adapted to fit snuggly and/or tightly over the end of the pre-applied tip 70 such that the combined cap and pulling tab 130' may be placed onto the end of the pre-applied tip 70 to substantially close it, as illustrated in FIG. 4C.

Figure 4D:
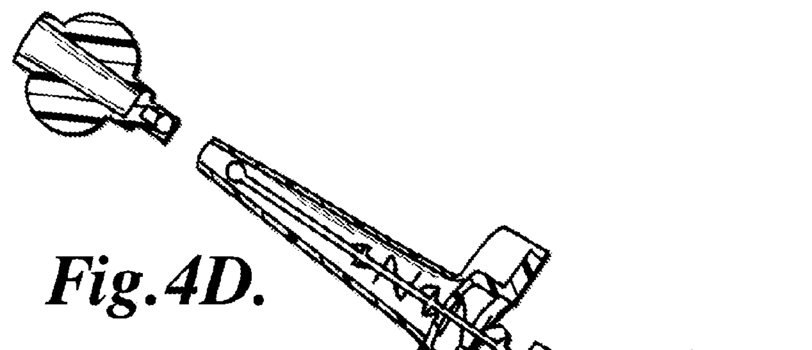
FIG. 4D is a partial exploded cross-sectional view of the double-barreled syringe assembly of FIG. 4.

In some embodiments, the syringe body 10, tip 70, static mixing element 82 and combined cap and pulling tab 130' may be formed as separate elements that may be assembled prior to deliver to a customer, as illustrated with the partial exploded view in FIG. 4D.

In other embodiments, the above components may be integrally combined in various combinations including, but not limited to, the combined cap and pulling tab and the static mixing element and/or any other suitable combination.

In some embodiments, the attachment of the tip may be accomplished by means of the previously discussed mating formations illustrated in FIGS. 1-3. In other embodiments, other attachment methods may be utilized, including, but not limited to, adhesive attachment, friction fit attachment, threaded screw in attachment, fusing (e.g. melting), and/or any other appropriate attachment method.

Figure 5:
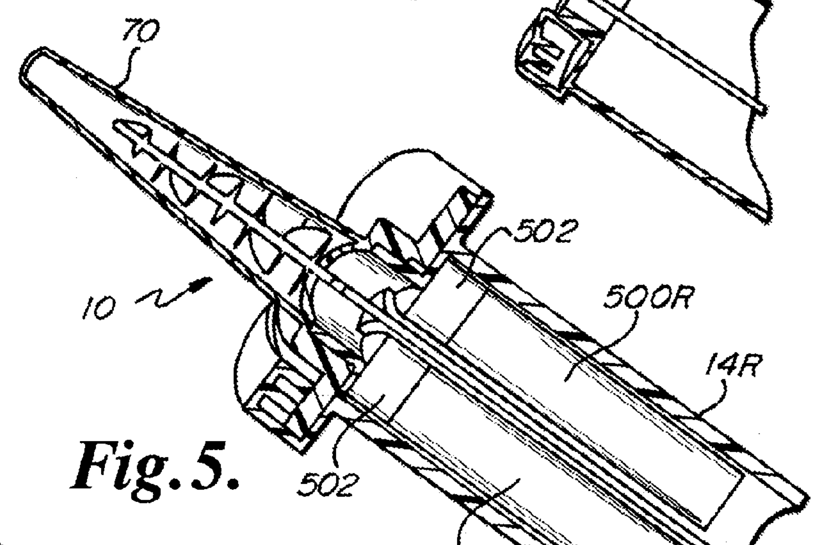
FIG. 5 is partial cross-sectional perspective view of a double-barreled syringe assembly with an inert material.

In other aspects, after the cap plugs 82R and 82L are removed from the outlets 24R and 24L, the syringe may include further means of segregating the contents of the separate barrels before intended use. In one aspect, as illustrated in the partial cross-sectional view of FIG. 5, the barrels 14R, 14L of the syringe body 10 may be at least partially filled with inert material 502 at the end proximal to the tip 70. The composition components 500R, 500L, which may be mixed to form an active admixture, may substantially fill the remainder of the internal space of the barrels 14R, 14L, respectively. The inert material 502 may substantially act as a barrier that may effect the substantial segregation of the composition components 500R, 500L and may be in direct contact with the components 500R, 500L, which may result in a layered effect within the barrels 14R, 14L, respectively. The inert material 502 may be removed to allow interaction of the components 500R, 500L to form an active admixture by means of applying a force onto the contents of the barrels 14R, 14L using the plungers 38R, 38L, respectively, in the manner discussed above.

The inert material 502 may be any material that may act as a barrier against the composition components 500R, 500L. The inert material 502 may, for example, resist mixing, reacting and/or otherwise not interact with the components 500R, 500L and may be a gel or other high viscosity fluid, a deformable solid, a packed powder, and/or any other suitable material type. Examples of suitable materials may include, but are not limited to, saccharide polymer gels such as agar, agarose, pectin and alginate, protein polymer gels such as gelatin, silicone, oil, petroleum jelly, and cationic polymer gels such as polyvinylpyrrolidone, polyvinyl alcohol and cellulosic material such as hydroxypropyl cellulose.

The presence of an inert material 502 may also aid in the use of the syringe 10 and the dispensing and/or mixing tip 70 by, for example, filling flow voids within the dispensing and/or mixing tip 70, which may allow a greater proportion of the active composition to be dispensed rather than being wasted inside the tip.

In some embodiments, at least a portion of the barrels 14R, 14L proximal to the tip 70 may be filled with an inert material 502. In other embodiments, at least a portion of the interior of the tip 70 may also be filled with an inert material 502.

Figure 5A:
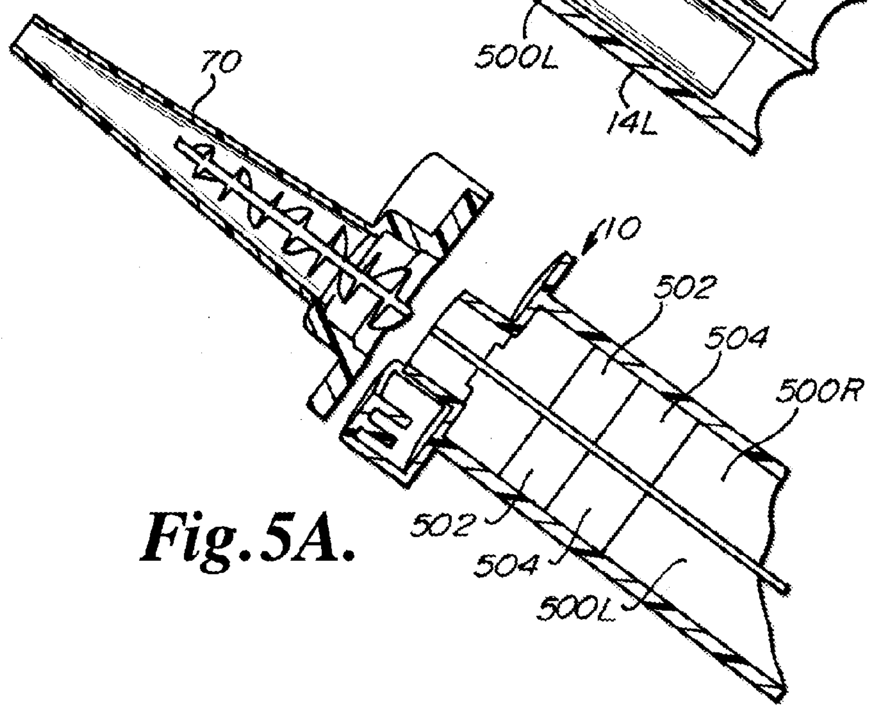
FIG. 5A is partial cross-sectional exploded view of a double-barreled syringe assembly with an inert material.

In still other embodiments, the inert material 502 may be spaced internally from the composition components 500R, 500L within the barrels 14R, 14L, respectively, by the space or gap 504, as illustrated in the partial cross-sectional exploded view of FIG. 5A.

Figure 5B:
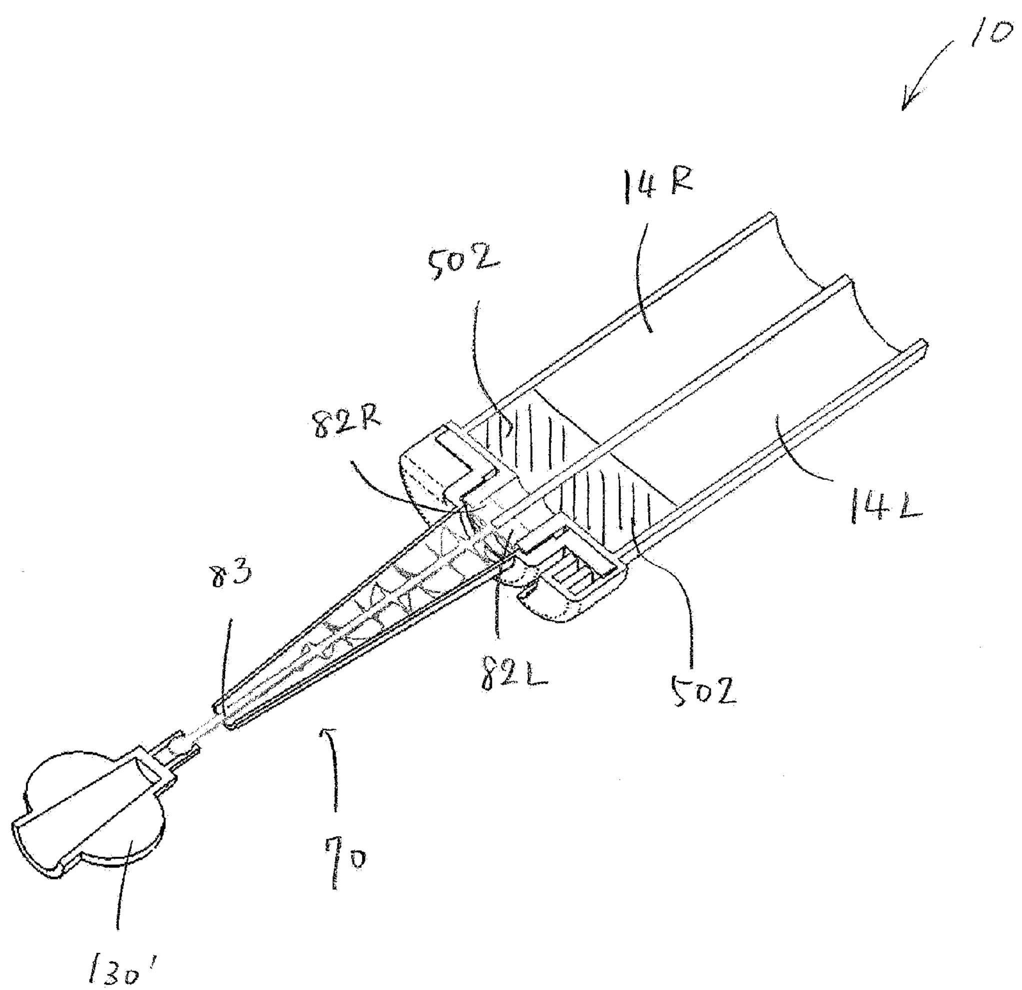
FIG. 5B is partial cross-sectional exploded view of a double-barreled syringe assembly with a combined cap and pulling tab, and an inert material.

In another embodiment, as exemplified in FIG. 5B, the tip may include a cap and a plug shape element adapted to be disposed inside the cap. A mixing element is attached and integral with the plug shape element, and maybe adapted for introducing the plug shape element into the barrel region of the syringe body. The pocket or hollow interiors of the barrel or barrels may have a corresponding feature for receiving the plug shape element so that the exit openings of the barrel or barrels may be closed by the plug shape element. The cap of the tip may also include, for example, threads adapted for attaching to the barrel or barrels by screwing onto the base thereof and a ledge for pushing the plug element on the mixing element onto the pocket or pockets of the barrel or barrels, closing the openings. The barrels 14R, 14L of the syringe body 10 may be at least partially filled with inert material 502 at the end proximal to the tip 70. Once the user applies appropriate external force to break the pull shaft 83

(preferably at the breaking point 83a) and effects the removal of the cap plugs 82R and 82L by pulling on the combined cap and pull tab 130', the inert material 502 may be removed to allow interaction of the components 50OR and 500L to form an active admixture by means of applying a force onto the contents of the barrels 14R and 14L using the plungers 38R, 38L, respectively, in the manner previously discussed.

In another embodiment, the tip may include a mixing element adapted to be disposed inside the tip and a separate plug element adapted for fitting into the exit opening end of the barrel or barrels. The plug element may be forced into place on the barrel or barrels by attachment of the tip.

In another aspect, the features may include seals that may be forced and/or broken so as to allow the contents of a compartment to exit.

In one embodiment, a seal, such as a foil seal, a wax paper seal or a polymeric film seal, may be introduced at the top of the barrel or barrels to seal off the content or contents. The seals may be adhesively coated for attachment to, for example, the top of the barrels. A formation, for example, a pointed formation, is adapted for breaking the seal may be introduced to the barrel or barrels before the barrel or barrels are filled with compositions. During use, the user may push on the plunger or plungers, driving the formation through the foil to open the barrel or barrels.

Figure 6:
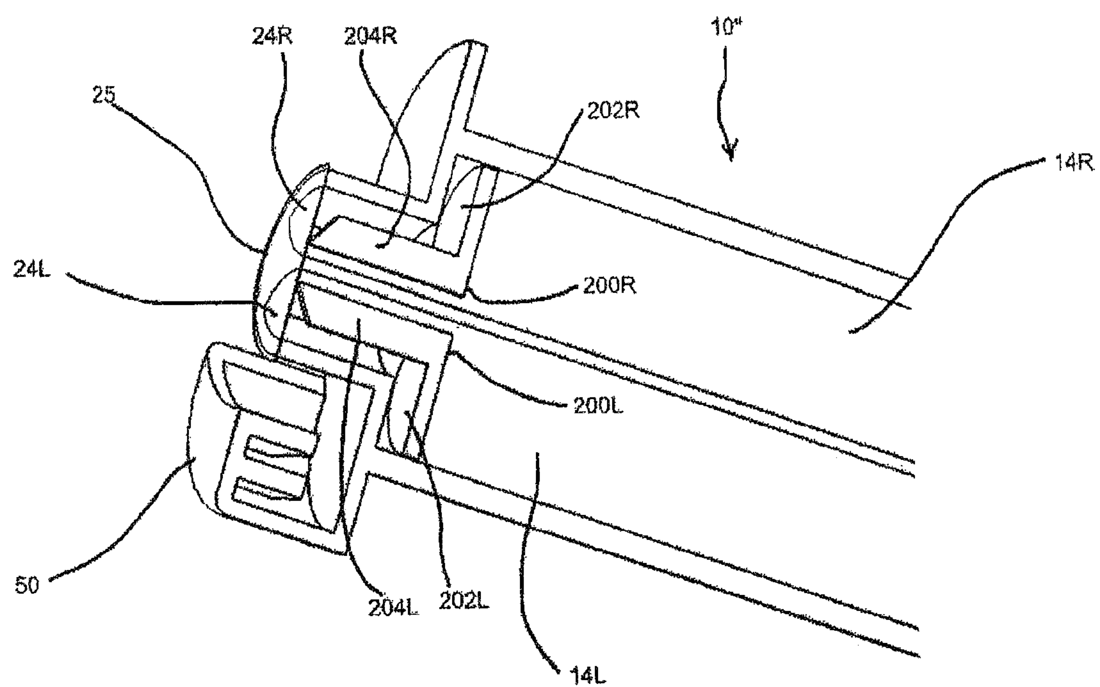
FIG. 6 is a partial cross-sectional perspective view of a double-barreled syringe assembly with a seal and seal breakers.

In another embodiment, a removal seal which may be a foil seal, for example, may be introduced at the top of the barrel or barrels to seal off the content or contents, as exemplified in FIG. 6. The barrel or barrels may be modified to include a cap which may be attached to the barrel or barrels with a living hinge. The cap may include a mixing element and adapted for attaching onto the opening end of the barrel or barrels. When the seal is removed, the cap may be onto the barrel or barrels for use.

In another aspect, the segregation of the composition components within the barrels of a syringe may be accomplished by introducing a seal over the outlet ports of the barrels, as exemplified in FIGS. 6 and 6A. The seal may substantially close off the outlet ports of the barrels and may preserve the segregation of the composition components by substantially sealing the surfaces of the outlet ports and a dividing formation, such as a septum, as discussed previously. The syringe may also include features, for example, formations, that may allow the user to remove and/or break the seal. Such features may be included in any appropriate position and/or location in the syringe 10" such that they may effect the removal and/or breakage of the seal 25, including, but not limited to, inside the barrels and between the outlet ports and the tip and/or mixing element, in close proximity to the seal.

FIG. 6 illustrates the use of a seal 25 over the outlet ports 24R, 24L of the barrels 14R, 14L of a syringe 10". In embodiments with a pre-applied tip (not shown), the syringe 10" may include features that may allow the user to remove and/or break the seal 25 without removing the tip to gain access to the seal 25, as noted above.

In an exemplary embodiment, the syringe 10" may include substantially identical seal breakers 200R, 200L, which may be adapted to lie within the chambers of the barrels 14R, 14L, respectively. The seal breakers 200R, 200L may include formations that may allow them to both break the seal 25 when a correctly applied force is introduced and may also include formations that may allow them to utilize an applied force from the user. The paddle-like portions 202R, 202L of the seal breakers 200R, 200L, respectively, may be adapted to substantially lie perpendicular to the long axis of the barrels 14R, 14L and may substantially occupy a significant proportion of the cross-sectional area of the interior space of the barrels 14R, 14L such that when a force is applied by the user to the plungers (not shown), the force may be transmitted to the paddle-like portions 202R, 202L via the contents of the barrels 14R, 14L such that the seal breakers 200R, 200L may move towards the outlets 24R, 24L.

FIG. 6A shows a perspective view of a seal breaker 200, which may be utilized in either barrel 14R, 14L of the syringe 10" as 200R or 200L, respectively. The seal breakers 200R, 200L may further include seal piercing formations 204R, 204L, respectively that, when the seal breakers 200R, 200L are moved sufficiently toward the outlets 24R, 24L, the seal piercing formations 204R, 204L may substantially displace and/or break the seal 25, which may allow the contents of the barrels 14R, 14L to exit through the outlets 24R, 24L.

The formations 204R, 204L may include substantially pointed and/or sharp leading portions 205R, 205L that may allow them to effectively pierce the seal 25 when an appropriate force is applied, as illustrated.

In some embodiments, the paddle-like portions 202R, 202L may be substantially solid formations that may occupy only a portion of the total cross-sectional area of the barrels 14R, 14L such that the contents of the barrels 14R, 14L may still flow past the paddle-like portions 202R, 202L at, for example, cut-out areas 203R, 203L, as illustrated.

In other embodiments, the paddle-like portions 202R, 202L may include perforations and/or other features, for example, formations, that may allow the contents of the barrels 14R, 14L to flow more freely through and/or past the paddle-like portions 202R, 202L.

In still another aspect, the syringe may include features, for example, formations, that may allow the outlets of the barrels to be substantially opened and closed multiple times during the course of use. The opening and closing of the outlets may be accomplished substantially with the tip pre-applied and remaining on the syringe. The syringe may include, for example, a system that may allow the user to manually open and close the outlets of the barrels by actuating a portion of the syringe.

In an exemplary embodiment, as exemplified in FIG. 7 the syringe manual control system 700 may include spatially separated outlet ports 712R, 712L on the end of the barrels 710 proximal to the tip. The top surface 711 of the end of the barrels 710 may include stop pair bars 714, 716, which may lie substantially at 90 degree intervals about the center of the top surface 711 on the perpendicular axes A, B, where pair 716 may lie substantially adjacent to the outlets 712R, 712L on axis B such that the sides of the top surface 711 corresponding to the outlets 712R, 712L may be symmetrical with respect to axis A. The stop pair bars 714, 716 may be substantially perpendicular to the top surface 711 and may be taller than the outlet ports 712R, 712L.

A switching disc 720 may be included and may provide the open and closed states of the outlets 712R, 712L. The switching disc 720 may include apertures 722R, 722L which may, in one alignment, provide clear openings to the outlets 712R, 712L below. The switching disc 720 may further include a sealing surface 723 on the side that faces the outlets 712R, 712L. The sealing surface 723, when in contact with the outlets 712R, 712L, may serve to substantially seal and/or block the outlets 712R, 712L such that the contents of the barrels of the syringe may be substantially contained and segregated. The sealing surface 723 may also provide a frictional and/or other holding force that may substantially limit free rotation of the switching disc 720 without the application of force by the user.

The switching disc 720 may also include stop pair bars 726, which may extend from the edge of the switching disc 720 in a direction substantially perpendicular to the radial axis of the switching disc 720. The stop pair bars 726 may lie substantially opposite each other with approximately 180 degree spacing about the center of the switching disc 720 and may be slightly offset from the symmetric axis B.

An axial shaft 730 may also be included and may interact with the switching disc 720 and the top surface 711 of the barrels. Axial holes 718, 728 may be included in the top surface 711 and switching disc 720, respectively, to accommodate the axial shaft 730. The axial shaft 730 may, for example, in some embodiments, be integral to the static mixing element and may substantially extend beyond the tip (not shown) such that the shaft 730 may be accessible to the user without removal of the tip. The axial shaft 730 may further include interfacing formations 731, 732 that may interface with corresponding formations 724 of switching disc 720. The interface between formations 731, 732 and 724 may substantially lock the switching disc 720 and the axial shaft 730 together, such that rotation of the axial shaft 730 may affect a substantially identical rotation of the switching disc 720.

Figure 7A:
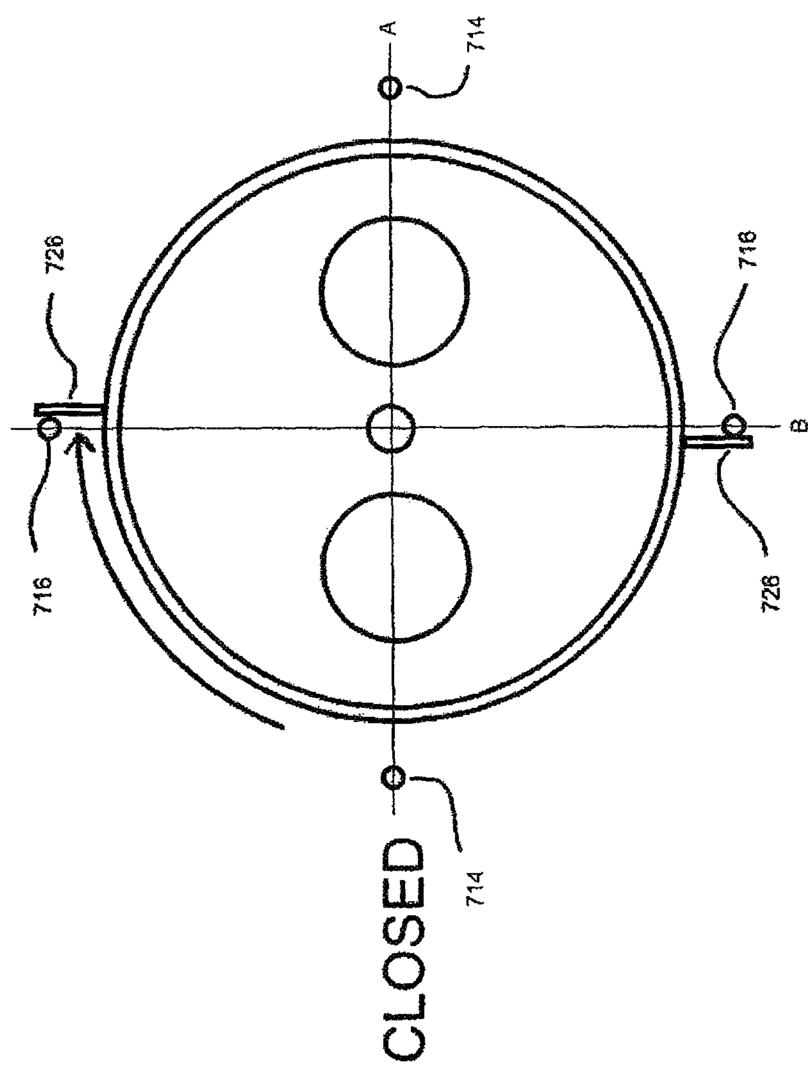
FIG. 7A is a top view of the double-barreled syringe manual control system of FIG. 7 in the closed alignment.
Figure 7B:
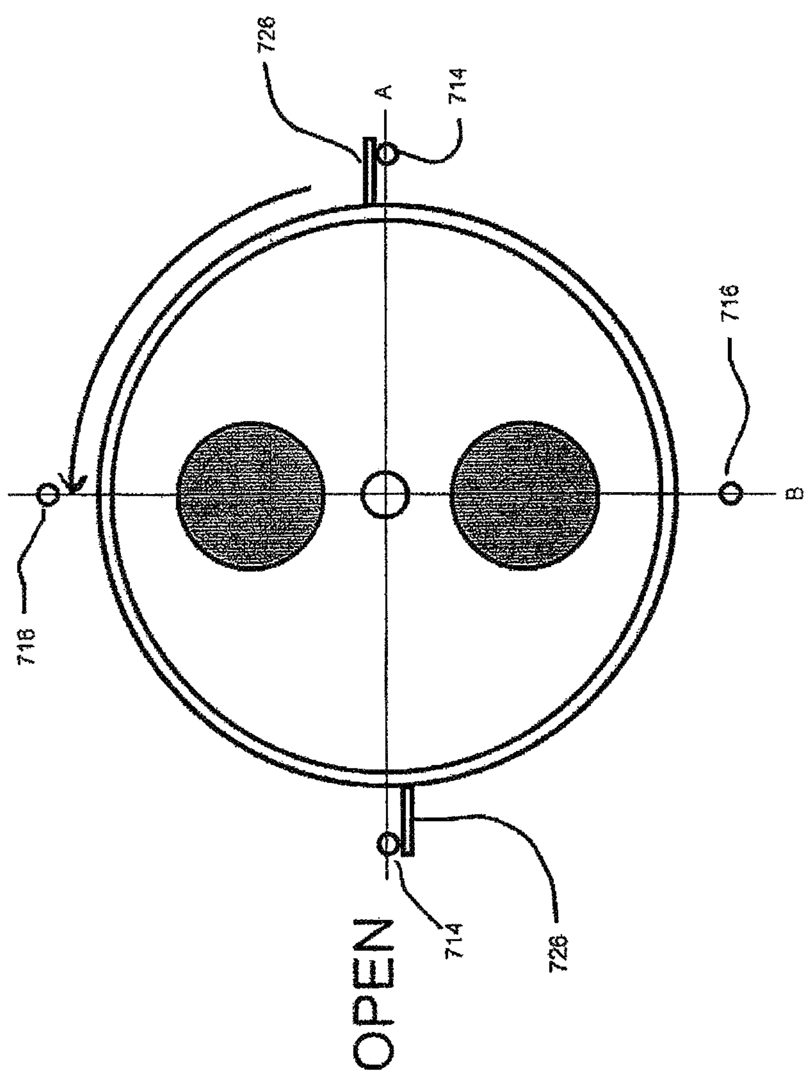
FIG. 7B is a top view of the syringe manual control system of FIG. 7 in the open alignment.

When assembled, the switching disc 720 may lie in substantially two alignments with the top surface 711, closed, as shown in the top view of FIG. 7A, and open, as shown in the top view of FIG. 7B. In the closed configuration of FIG. 7A, the switching disc 720 may be rotated such that the apertures 722R, 722L are 90 degrees misaligned from the outlets 712R, 712L (obscured by the switching disc 720). The stop pair bars 726 may prevent further rotation in the counterclockwise direction by stopping against the stop pair bars 716 of the top surface 711. The alignment may be changed to the open alignment, as shown in FIG. 7B, by rotating the switching disc 720, for example, in the clockwise direction.

In the open configuration, the apertures 722R, 722L may align with the outlets 712R, 712L such that the contents of the barrels may exit through the openings (as indicated by the shaded regions). The stop pair bars 726 and the axial shaft 730 may be utilized by the user to effect a change in the alignment of the switching disc 720 by rotation in a given direction.

In another embodiment, the directional orientations of the various components may be reversed such that clockwise rotation of the switching disc 720 closes the outlets 712R, 712L and counterclockwise rotation opens them.

In some embodiments, the apertures 722R, 722L may be substantially the same size and shape as the outlets 712R, 712L. In other embodiments, apertures 722R, 722L may be of a different size and shape than the outlets 712R, 712L.

In other embodiments, the outlets 712R, 712L may be flush with the surface of top surface 711 and the switching disc 720 may lie directly on the top surface 711. The switching disc 720 may also include formations that may lock it and/or otherwise fix it to the top surface 711 with respect to vertical and/or horizontal movement such that the switching disc 720 may still rotate freely about the central axis.

In still other embodiments, the components of the system 700 may be of any shape and/or size that may effect the desired operation of the system 700.

In yet other embodiments, the outlets 712R, 712L may be adjacent in a unified column, such as in the syringes described previously. In such embodiments, the portion of the syringe 710 may be an adapter that may be included such that the outlets 712R, 712L may be spatially separated such that the resultant top surface may appear as shown in FIGS. 7, 7A and 7B.

Figure 8:
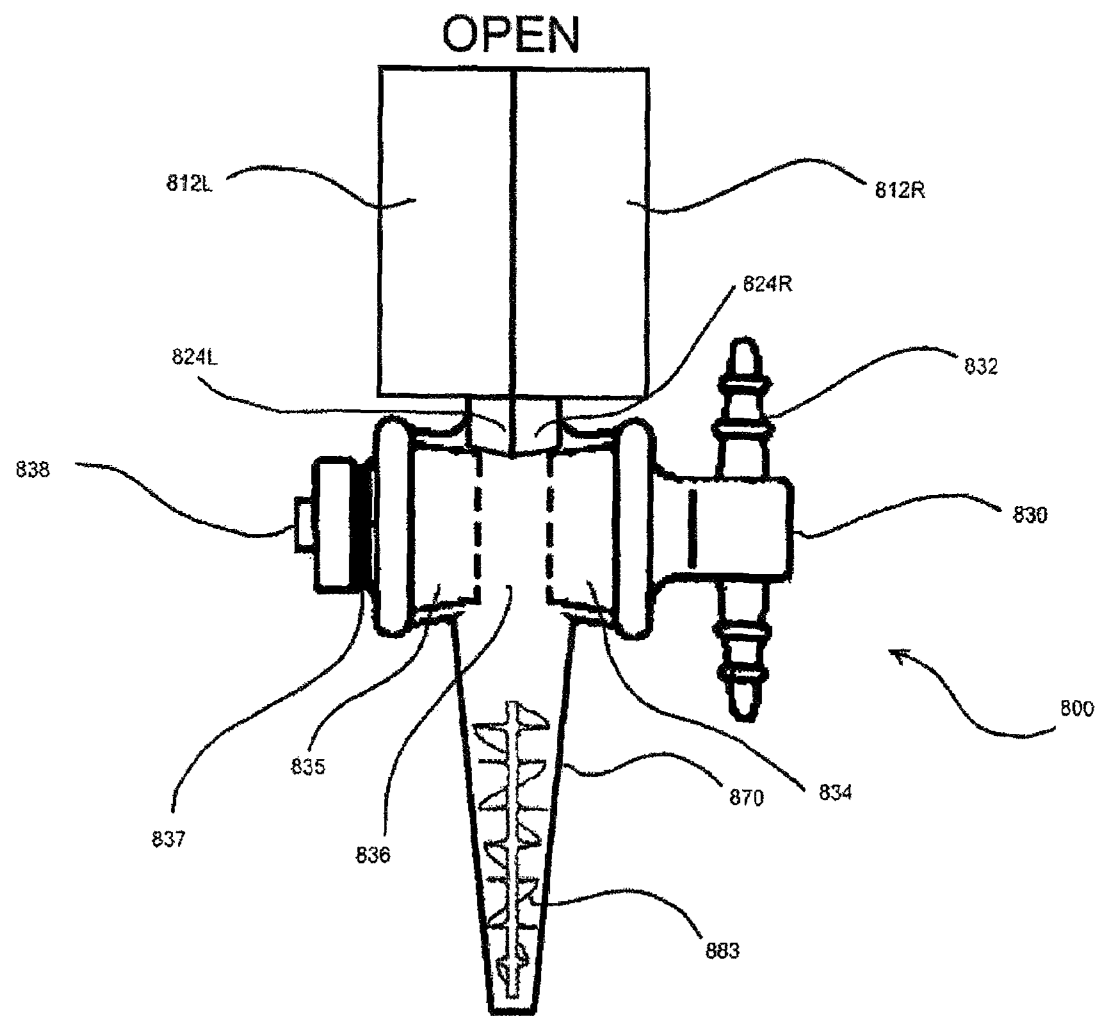
FIG. 8 is a partial cross-sectional view of a double-barreled syringe assembly with a stopper system in the open alignment.

In another exemplary embodiment, the syringe may include a stopper system that may serve to control the open and closed states of the outlets of the barrels. FIG. 8 is a partial cross-sectional view of a double-barreled syringe system 800 with a pre-applied tip 870. In one embodiment, the tip 870 may be permanently attached or integrally formed with the syringe. In another embodiment, the tip 870 may be detachable. The syringe system 800 may include barrels 812R, 812L with outlets 824R, 824L, respectively. The pre-applied tip 870 may include within it a static mixing element 883, which may operate in a manner similar to the static mixing elements discussed above.

The stop pair bars 726 may prevent further rotation in the clockwise direction by stopping against the stop pair bars 714 of the top surface 711. The alignment may be changed to the closed alignment, as shown in FIG. 7A, by rotating the switching disc 720 in the counterclockwise direction.

The syringe system 800 may also include a stopper system 830 that may be adapted to substantially open and close the outlets 824R, 824L of the barrels 812R, 812L. The stopper system 830 may include a cylinder 834, which is illustrated in FIG. 8B, with perpendicular bore 836 that may pass through the cylinder 834 and may define two openings on opposite sides of the surface of the cylinder 835. The bore 836, when in the open alignment, as illustrated in FIG. 8, may serve as an opening to the outlets 824R, 824L and may allow the contents of the barrels 812R, 812L to exit through the outlets 824R, 824L to the tip 870 and static mixing element 883. The cylinder 834 of the stopper system 830 may be rotated about its axis by actuating handle 832. An adjustment nut 838 may also be included to allow tightening and/or loosening of the rotation of the cylinder 834. A gasket 837 may provide cushioning of the nut 838 against the housing of the stopper system 830 and may aid in maintaining the tightness of the adjustment to the cylinder 834.

Figure 8A:
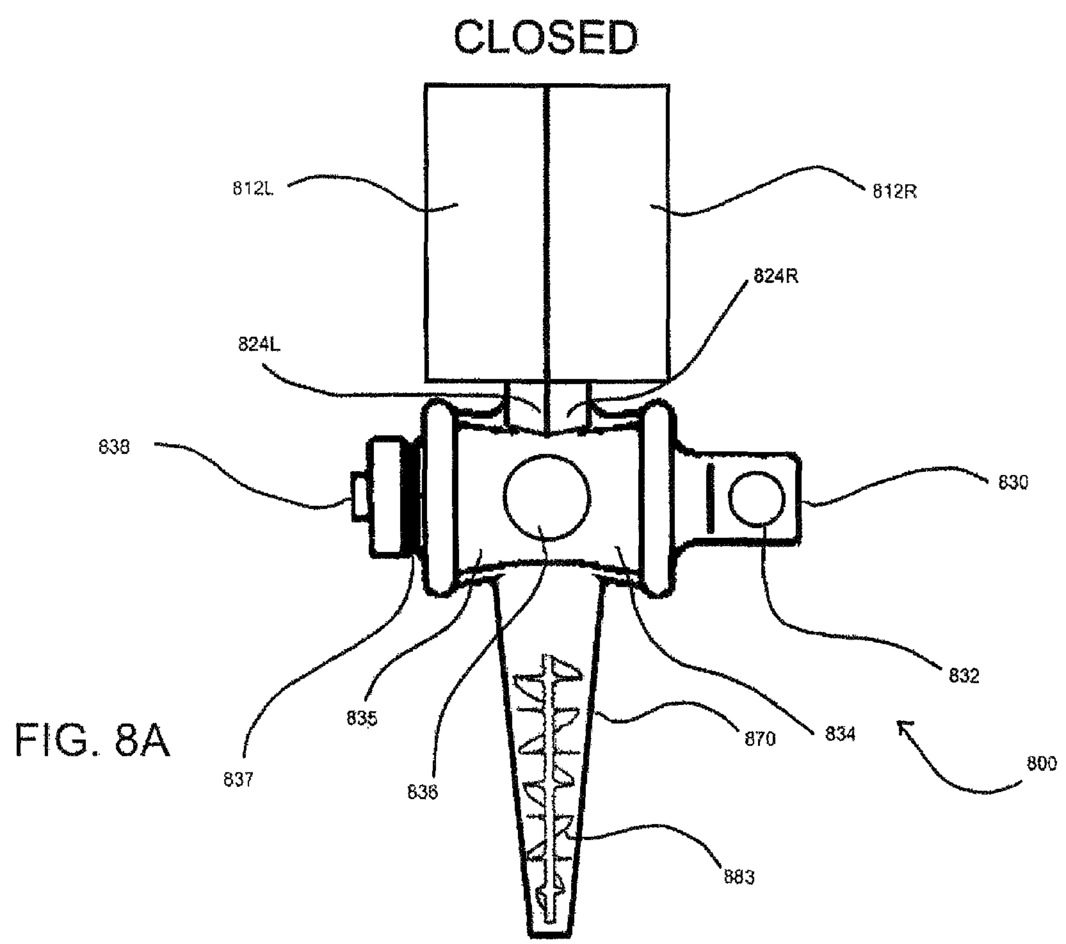
FIG. 8A is a partial cross-sectional view of a double-barreled syringe assembly with a stopper system in the closed alignment.
Figure 8B:
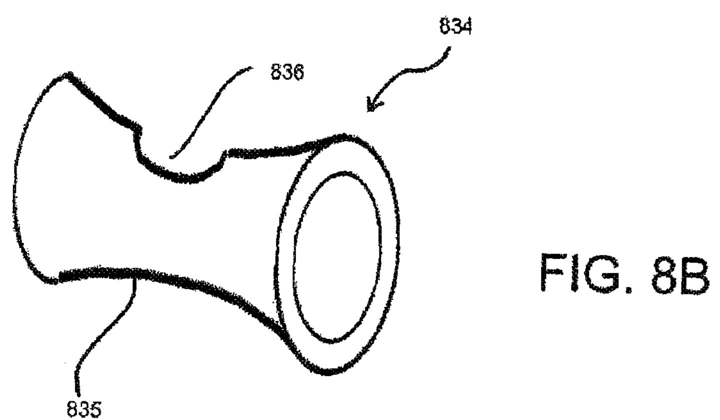
FIG. 8B is a perspective view of a stopper cylinder of FIGS. 8 and 8A.

The handle 832 may be rotated from the open alignment by rotation in either the clockwise or counterclockwise direction to yield a closed alignment, an example of which is illustrated in FIG. 8A. The surface 835 of the cylinder 834 may be contoured in a manner corresponding to a curvature and/or other contour present on the outlets 824R, 824L of the barrels 812R, 812L. The corresponding contours may assure a tight seal between the surface 835 and the outlets 824R, 824L when in a closed alignment.

The components of the stopper system 830, in particular the cylinder surface 835 and the corresponding surfaces on the other components may be manufactured from and/or coated with a material that may be conducive to allowing free rotation of the components while still allowing for a tight and/or sealing fit at the outlets 824R, 824L. Examples of appropriate materials include, but are not limited to, fluoropolymers such as polytetrafluoroethylne (PTFE or Teflon), fluorinated-ethylene-propylene (FEP) and perfluoroalkoxy polymer resin (PFA), lubricants such as silicone grease, petroleum-based products such as oil, and/or any other appropriate material. The materials utilized in the stopper system may also be, in general, resistant to any chemicals present in the compositions of the contents of the barrels 812R, 812L.

Figure 10:
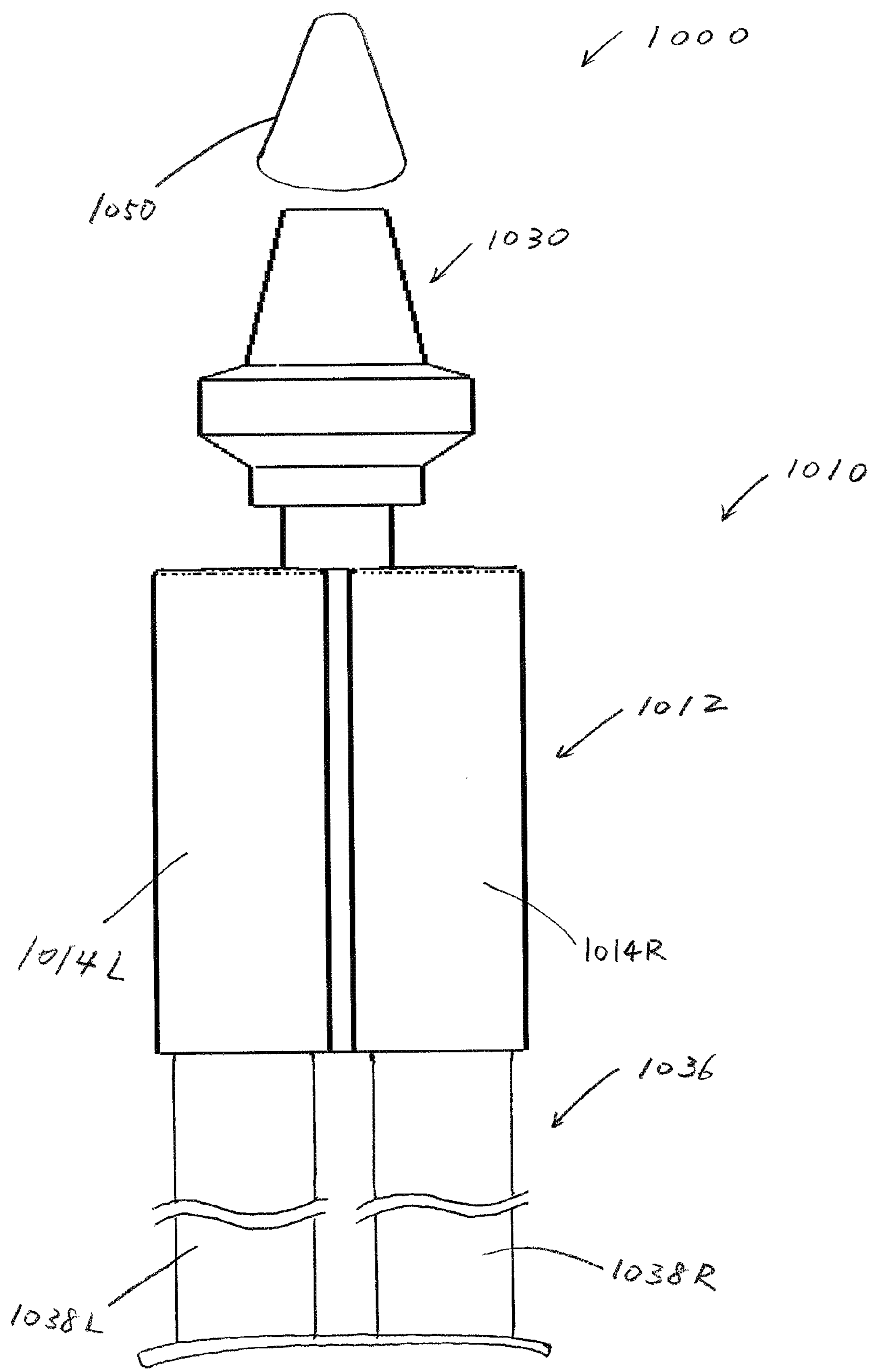
FIG. 10 is a perspective view of a double-barrel syringe with a rotatable head.
Figure 10A:
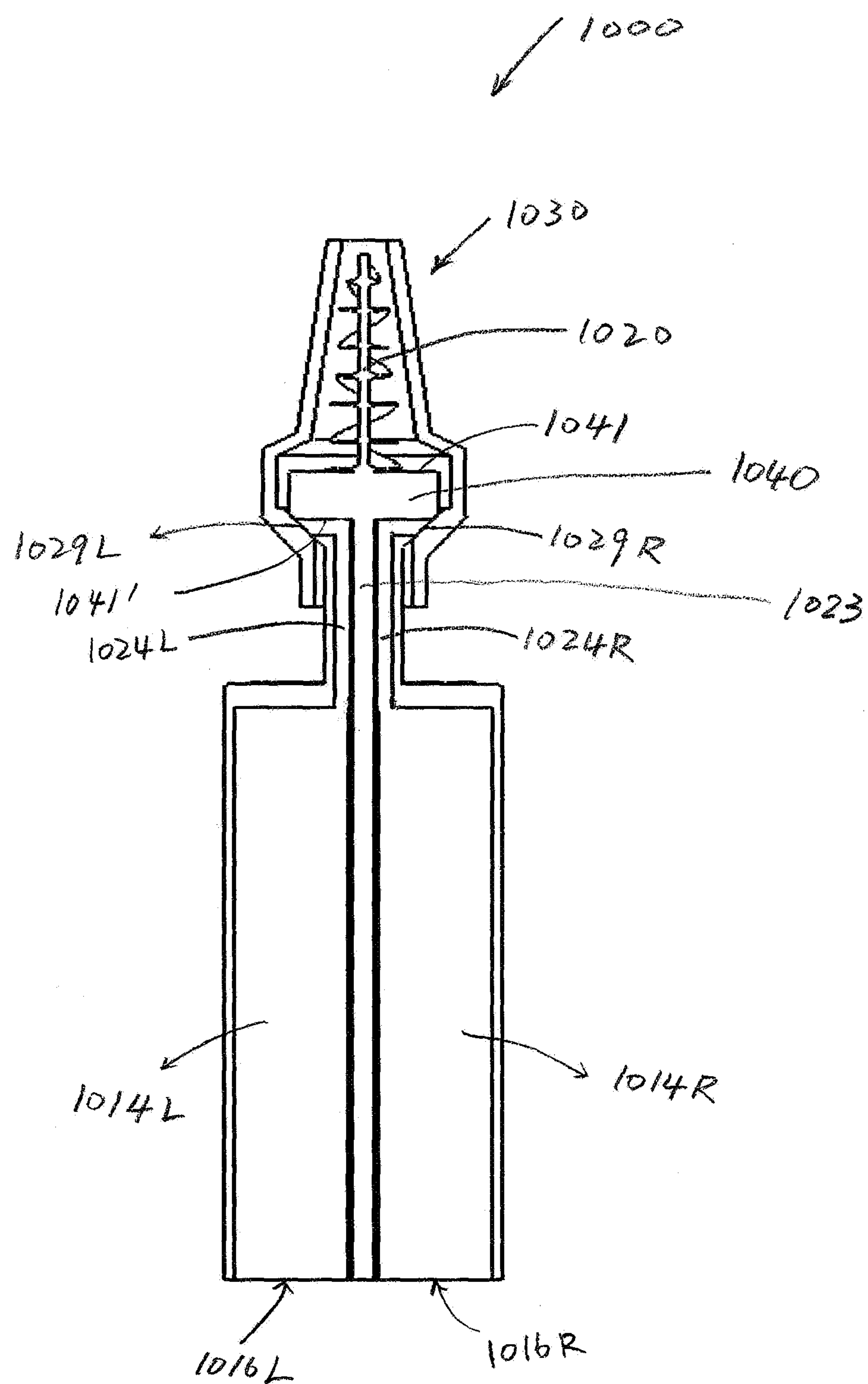
FIG. 10A is a cross-sectional perspective view of a double-barrel syringe with a rotatable head.

In another exemplary embodiment, a syringe may include a rotatable head that may serve to control the open and closed states of the outlets of the barrels. As shown in FIG. 10 and 10A, the syringe 1000 may include a syringe barrel 1010, a mixing element 1020 and a rotatable head 1030. The syringe barrel 1010 may include a double-barrel assembly 1012 that may have juxtaposed first and second generally cylindrical barrels 1014L, 1014R, which may have a common length and a generally cylindrical bore 1016L, 1016R, respectively. The syringe barrel 1010 may further include a double-plunger assembly 1036 that may have juxtaposed generally cylindrical first and second plungers 1038L, 1038R of a common length.

Figure 10B:
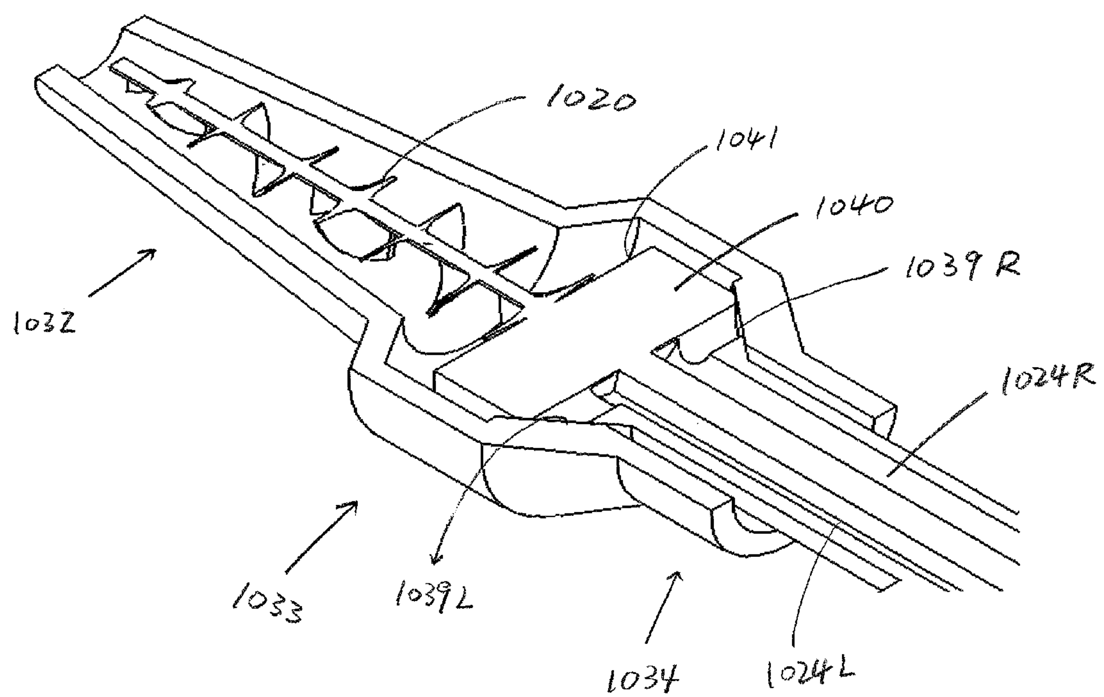
FIG. 10B is a partial cross-sectional perspective view of a double-barrel syringe focusing on the rotatable head.

As can be shown in FIGS. 10A and 10B, a pre-mixing neck portion 1023 may have juxtaposed first and second generally cylindrical connecting channels 1024L, 1024R, respectively. The connecting channels 1024L, 1024R are L-shaped, extending from outlets of the cylindrical barrels 1014L, 1014R, respectively, and ending at sealing surfaces 1039L, 1039R, respectively, of the rotatable head 1030. The sealing surfaces 1039L, 1039R are located at lower inner surfaces of the rotatable head 1030 and adapted to tightly seal discharge ends 1029L, 1029R of the connecting channels 1024L, 1024R, respectively, to prevent any premature interaction of the components in the barrels before mixing with each other.

Still referring to FIGS. 10A and 10B, the mixing element 1020 extends from a top surface 1041 of a base 1040, and at least portion of the bottom surface 1041' of the base 1040 forms portion of the inner surfaces of the connecting channels 1024L, 1024R, respectively. The L-shaped connecting channels 1024L and 1024R are located underneath the base 1040.

The mixing element 1020, the base 1040 and at least portion of the pre-mixing neck portion 1023 are encircled by the rotatable head 1030 which includes, for example, threads 1031 (not shown) adapted to attach to the pre-mixing neck portion 1023 by screwing onto corresponding threads 1031' (not shown) on the outer surface of the pre-mixing neck portion 1023 to adjust relative position between the discharge ends (1029L, 1029R) of the connecting channels (1024L, 1024R) and the sealing surfaces (1039L, 1039R). The rotatable head 1030 has a substantially hollow interior. In one embodiment, the rotatable head 1030 may form, when assembled properly, a tip portion 1032, an enlarged middle portion 1033 and a thread portion 1034.

Figure 10C:
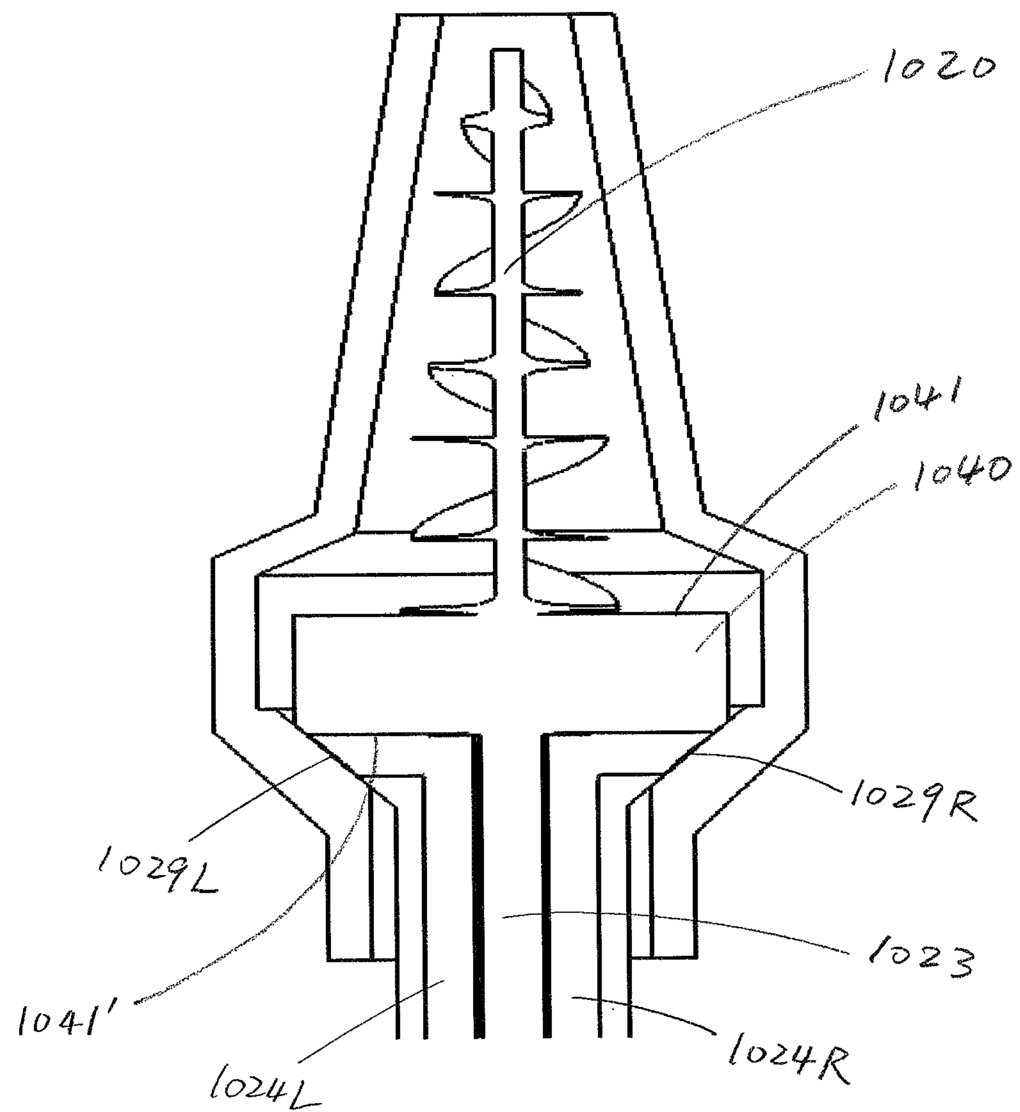
FIG. 10C is a perspective view of the double-barrel syringe with a rotatable head in a closed position.

Referring to FIG. 10C with respect to a closed position according to the embodiment, the connecting channels 1024L, 1024R, respectively, are sealed when the sealing surfaces 1039L and 1039R substantially entirely block the outlets of the connecting channels 1024L, 1024R, respectively. The seal is sufficiently tight that any premature interaction of components from barrels 1014L, 1014R (not shown), may be minimized or prevented. In addition, those skilled in the art may furthermore make either interface sealing surface and or the threads that seal below the sealing surface from a flexible sealing material in appropriate durometer or hardness, such as silicon, thermosetting rubber, polypropylene, high density polyethelene, polyurethane, thermoplastic elastomer such as synthetic rubber like Kraton polymers, polyvinyl chloride, thermoplastic silicon vulcanite, or melt processable rubber to furthermore aid in the sealing.

Figure 10D:
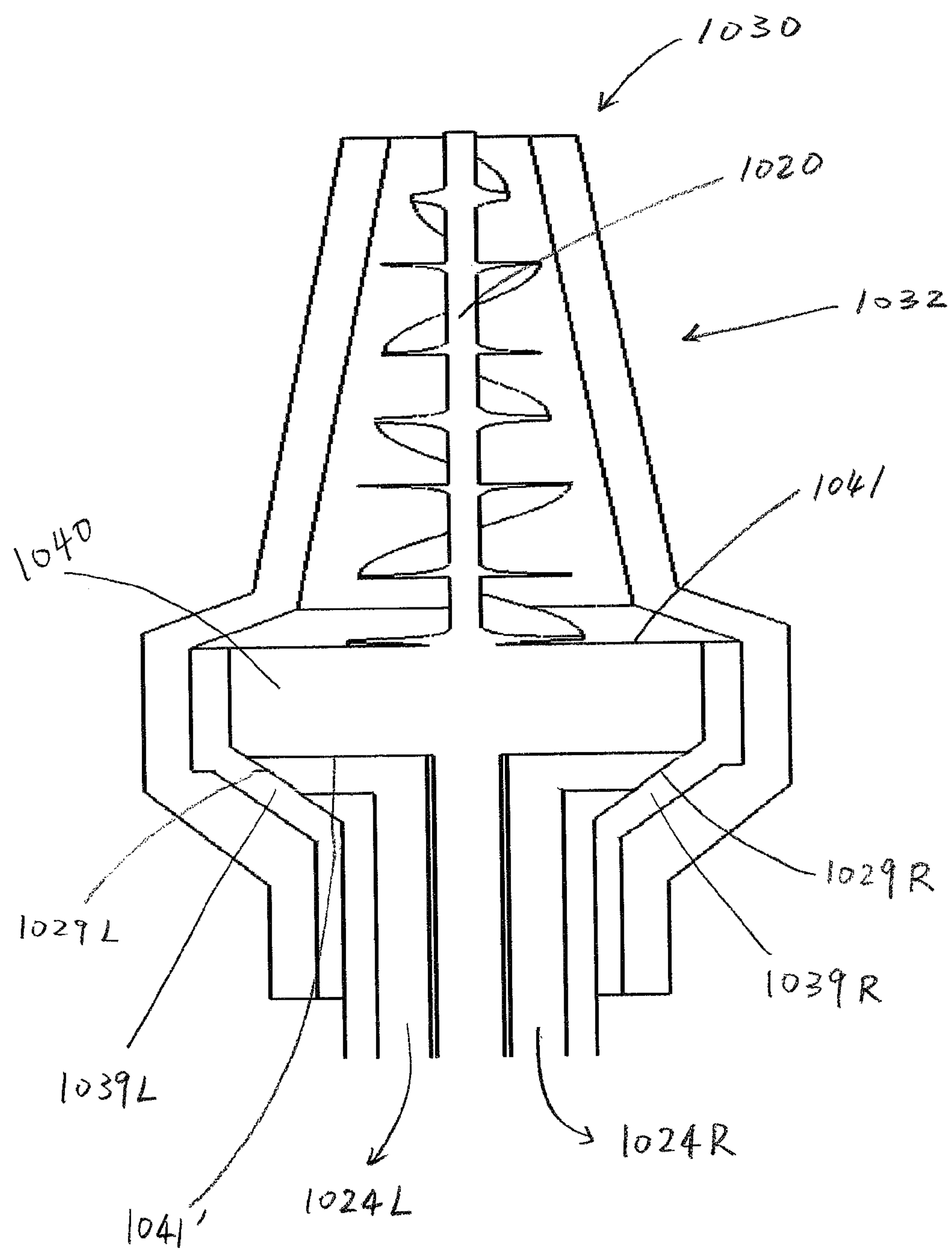
FIG. 10D is a perspective view of the double-barrel syringe with a rotatable head in an open position.

As can be seen in FIG. 10D, the relative position between the sealing surfaces (1039L, 1039R) and the discharge ends (1029L, 1029R) of the connecting channels (1024L, 1024R) may be changed by twisting the rotatable head 1030. Once the sealing surfaces 1039L and 1039R are moved away from the discharge ends 1029L and 1029R, the components in the barrels 1014L, 1014R (not shown), are allowed to move to the tip portion 1032 to form an admixture for dispensing.

For example, when the sealing surfaces (1039L, 1039R) are removed, the component in each barrel moves forward separately from each connecting channel to at least portion of the inner surface of the rotatable head 1030 before reaching the mixing element 1020, which may be closely received and wedged within the bore of the tapered portion of the rotatable head 1030. The components are mixed in the tip portion 1032 in the manner as previously discussed.

In some embodiments, the attachment of the rotatable head 1030 may be accomplished by means of clamping two identical halves to encircle the mixing element 1020, the base 1040 and at least portion of the pre-mixing neck portion 1023. In other embodiments, other attachment methods may be utilized, including, but not limited to, adhesive attachment, friction fit attachment, fusing (e.g. melting), and/or any other appropriate attachment method.

In some embodiments, the rotatable head 1030 may include a cap 1050 as shown in FIG. 10, which may also include, for example, threads (not shown) adapted for attaching to the tip portion 1032 of the rotatable head 1030 by screwing onto the outer surface of the upper tip portion 1032.

Figure 11:
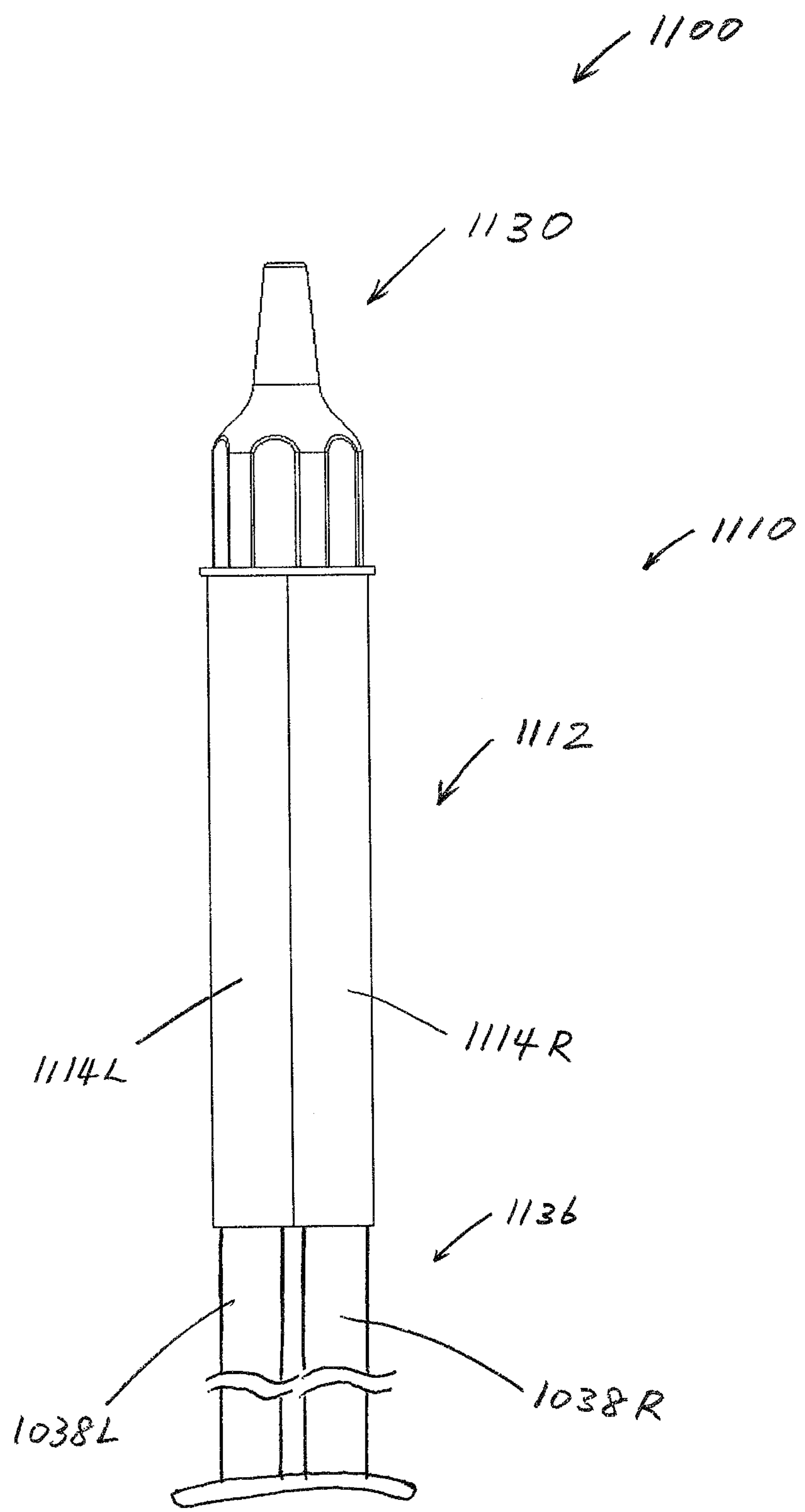
FIG. 11 is a perspective view of a double-barrel syringe including a rotatable mixing tip.
Figure 11A:
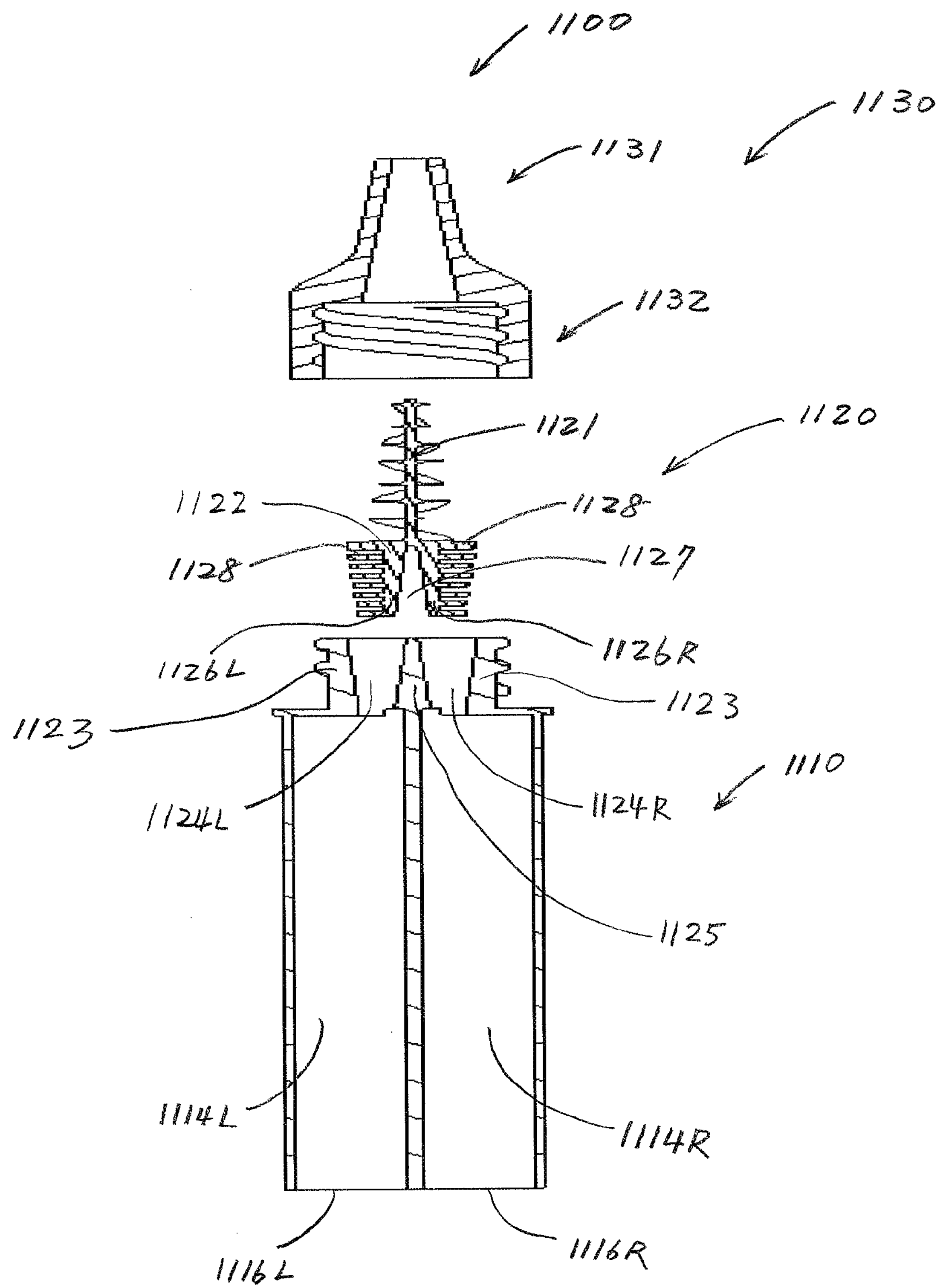
FIG. 11A is an exploded perspective view of the syringe in FIG. 11, including a mixing element with an integrated plug.

FIGS. 11 and 11A illustrates another exemplary embodiment of the syringe having a rotatable head. The syringe 1100 may include a syringe barrel 1110, a mixing and switching assembly 1120, and a rotatable mixing tip 1130. The syringe barrel 1110 may include a double-barrel assembly 1112 that may have juxtaposed first and second generally cylindrical barrels 1114L, 1114R, which may have a common length and a generally cylindrical bore 1116L, 1116R, respectively. The syringe 1100 may further include a double-plunger assembly 1136 that may have juxtaposed generally cylindrical first and second plungers 1138L, 1138R of a common length.

As can be seen in FIG. 11A, a pre-mixing neck portion 1123 may have juxtaposed first and second connecting channels 1124L, 1124R, respectively. The tapered connecting channels extend from the outlets of the cylindrical barrels 1114L, 1114R, respectively, to the discharge end of the neck portion 1123. The connecting channels (1124L, 1124R) may be spaced by a tapered protrusion 1125 adapted to securely hold the mixing and switching assembly 1120.

The mixing and switching assembly 1120 may include a mixing element 1121 and a plug 1122, wherein the mixing element 1121 and the plug 1122 are assembled together and the mixing element 1121 extends from the top surface of the plug 1122. The plug 1122 includes a right tapered unit 1126R and a left tapered unit 1126L, which are separated by a tapered vacancy 1127. Each tapered unit may include a plurality of fins 1128, arranged substantially in parallel, located thereat. The size and shape of taper units (1126L, 1126R) is designed to tightly fit the corresponding connecting channels 1124L, 1124R, respectively. When the mixing and switching assembly 1120 is pushed down and the pinnacle of the tapered protrusion 1125 reaches the tapered end of the tapered vacancy 1127, the left and right tapered units 1126L, 1126R, substantially block the connecting channels 1124L, 1124R, respectively, and a tight seal of each connecting channel is formed to prevent the component in each barrel from prematurely mixing with each other.

Figure 11B:
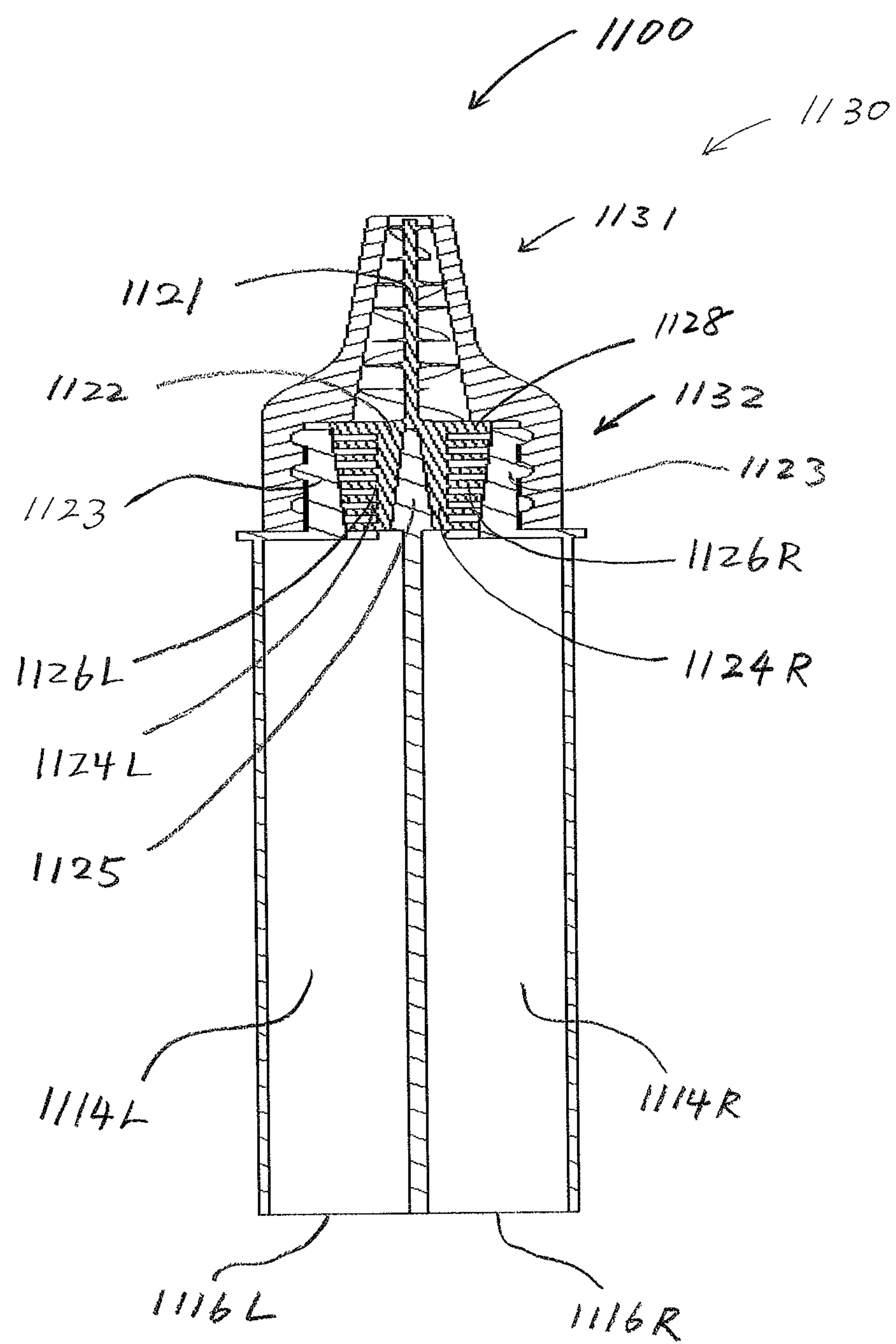
FIG. 11B is a partial cross-sectional perspective view of the syringe in FIG. 11 when the syringe is in its closed position.

Referring to FIGS. 11A and 11B, the mixing tip 1130 may include a tip portion 1131 and a thread portion 1132. The mixing element 1121 is closely received and wedged within the bore of the tapered tip portion 1131. The thread portion 1132 is adapted to attach to the pre-mixing neck portion 1123 by screwing onto portion of the outer surface thereof to control the position of the mixing and switching assembly 1120.

For example, when the mixing tip 1130 is screwed all the way down on the neck portion 1123, the syringe is at its closed position, and the upper portion of the thread in the thread portion 1132 engages with the upper portion fins of the tapered units to force the plug down to close the outlets of the barrels, as shown in FIG. 11B. An opened position may be achieved when a user makes an upward, for example, quarter or half turn of the mixing tip 1130 to disengage the mixing and switching assembly 1120. In other words, the mixing and switching assembly 1120 is freely suspended within the mixing tip 1130 after an upward quarter or half turn of the mixing tip 1130. Thus, when appropriate force is applied from the double-plunger assembly 1136 to the components in the barrels, the disengaged mixing and switching assembly 1120 is accordingly lifted away from the closed position to allow the component in each barrel to move toward the tip portion of the mixing tip 1130 for form an admixture for dispensing. The syringe in the present embodiment can be resealed simply by screwing down the mixing tip 1130 again.

Figure 12:
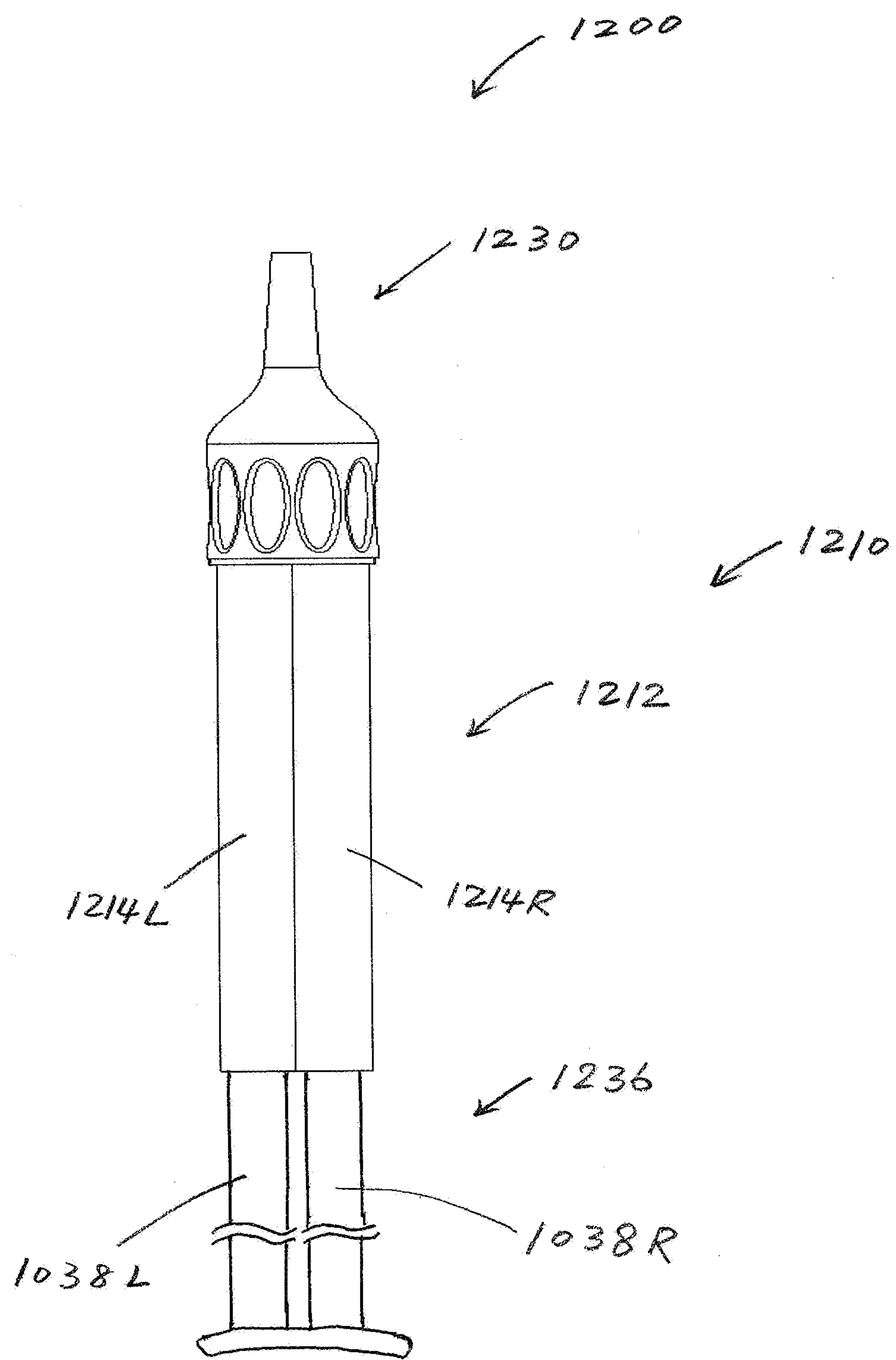
FIG. 12 is a perspective view of another double-barrel syringe including a rotatable mixing tip.
Figure 12A:
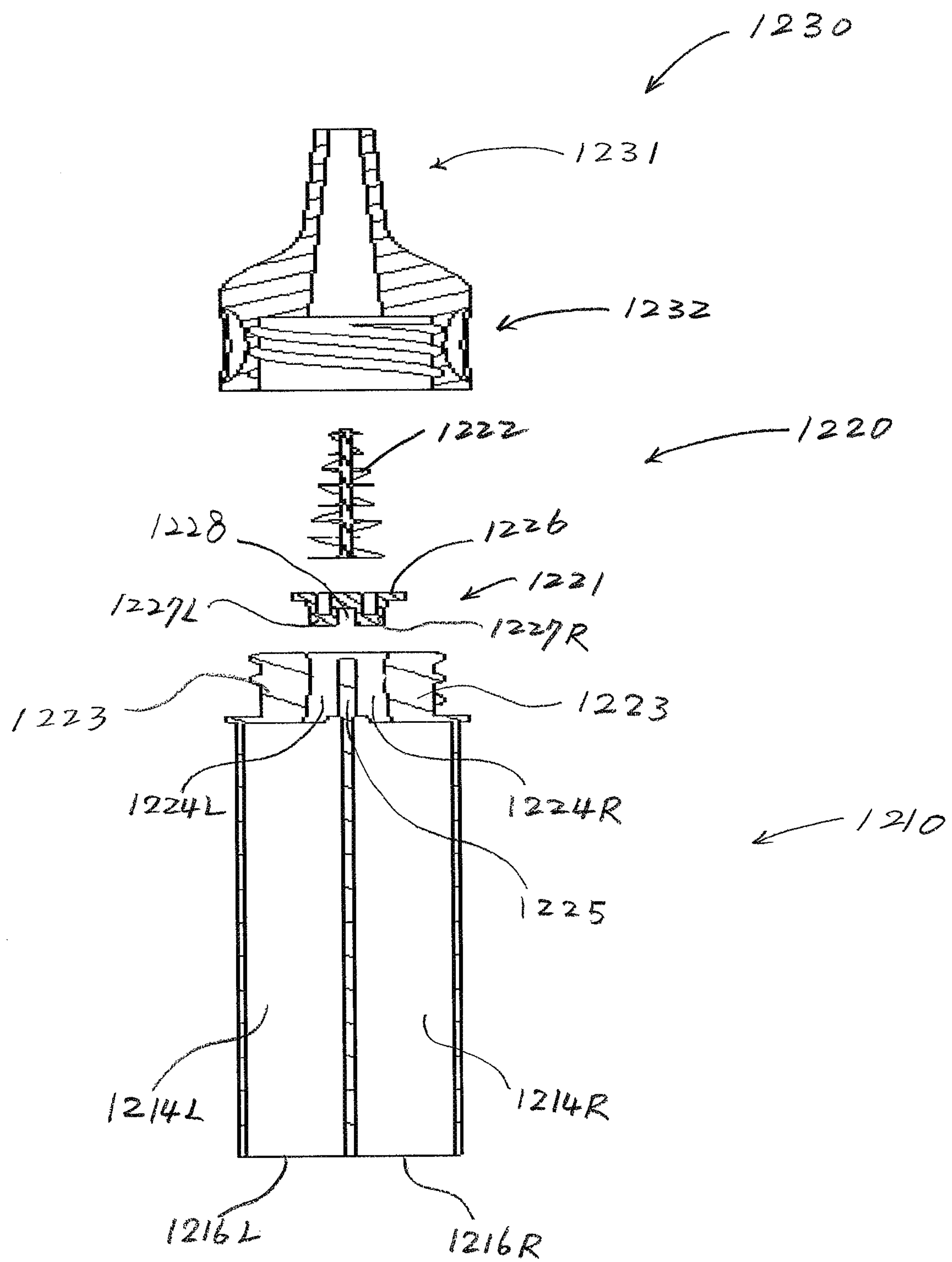
FIG. 12A is an exploded perspective view of the syringe in FIG. 12, including a mixing element with a separated plug.

In some aspects, the plug and the mixing element are not integrated together. As shown in FIGS. 12 and 12A, the syringe 1200 may include a syringe barrel 1210, a mixing and switching assembly 1220 including a plug 1221 and a mixing element 1222, and a rotatable mixing tip 1230. Likewise, the syringe barrel 1210 may include, fro example, a double-barrel assembly 1212 that may have juxtaposed first and second generally cylindrical barrels 1214L, 1214R, respectively, which may have a common length and a generally cylindrical bore 1216L, 1216R, respectively. The syringe barrel 1210 may further include, for example, a double-plunger assembly 1236 that may have juxtaposed generally cylindrical first and second plungers 1238L, 1238R of a common length.

Figure 12B:
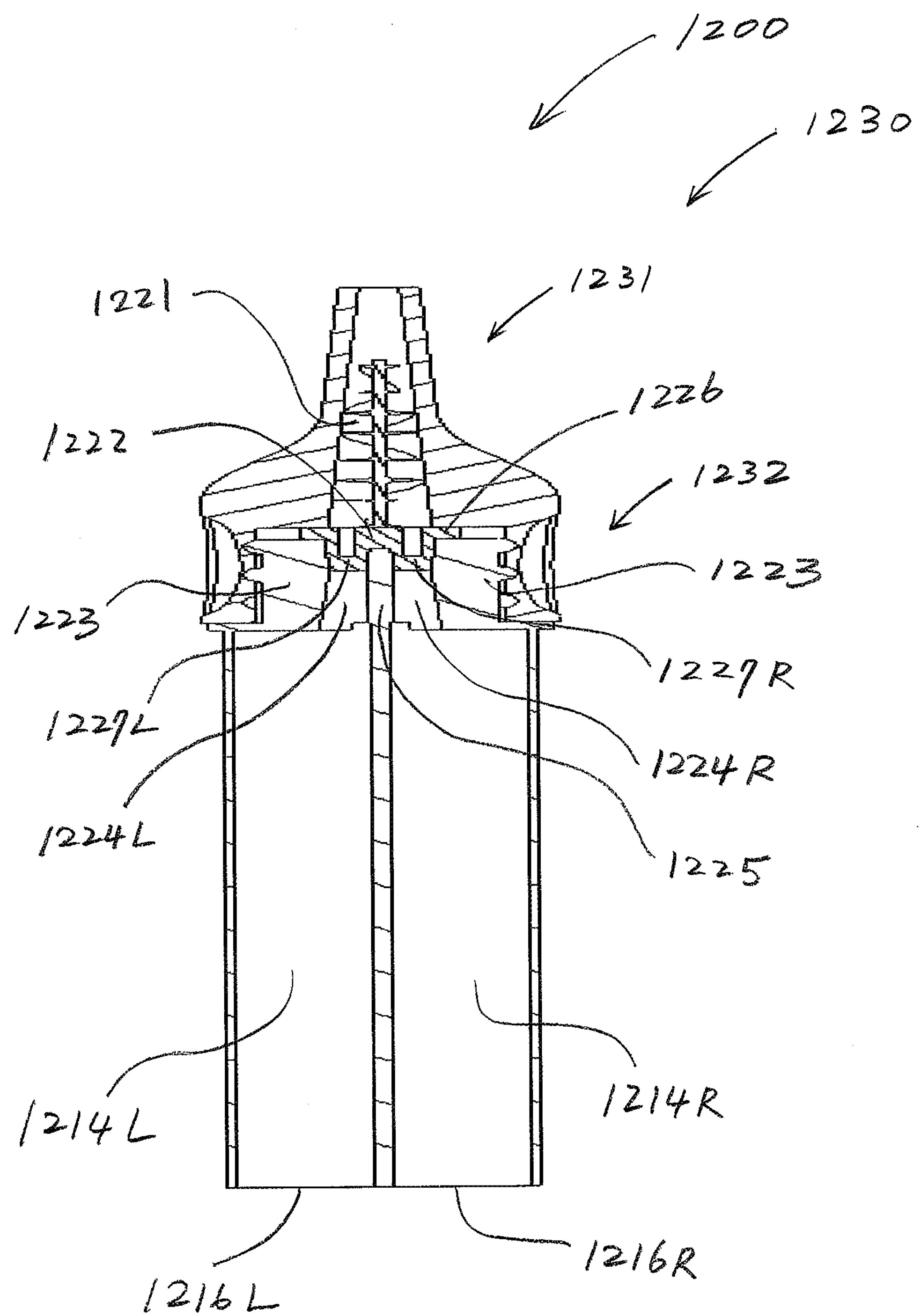
FIG. 12B is a partial cross-sectional perspective view of the syringe in FIG. 12 when the syringe is in its closed position.

Referring to FIG. 12A and FIG. 12B, a pre-mixing neck portion 1223 may have juxtaposed first and second connecting channels 1224L, 1224R, respectively. Each connecting channel extends from an outlet of each cylindrical barrel 1214L, 1214R, respectively, to the discharge end of the neck portion 1223. The connecting channels 1224L and 1224R are compartmentalized by a separation unit 1225, which is adapted to securely hold the plug 1221.

The plug 1221 includes a disc 1226, a right leg 1227R and a left leg 1227L, which extends downwardly from the disc 1226, and are separated by a vacancy slot 1228. The size and shape of each leg (1227L, 1227R) is designed to tightly fit the corresponding connecting channels 1224L, 1224R, respectively. When the plug 1221 is pushed down and the separation unit 1225 fully engages with the vacancy slot 1228, the left and right legs 1227L, 1227R, substantially block the connecting channels 1224L, 1224R, respectively, and a tight seal of each connecting channel is formed to prevent the components from premature mixing with each other.

The mixing tip 1230 may include a tip portion 1231 and a thread portion 1232. The mixing element 1222 is closely received and wedged within the bore of the tapered tip portion 1231. The thread portion 1232 is adapted to attach to the pre-mixing neck portion 1223 by screwing onto portion of the outer surface thereof to control the position of the plug 1221.

For example, when the mixing tip 1230 is screwed all the way down on the neck portion 1223, the syringe is at its closed position, and at least part of the thread portion 1232 engages with the disc 1226 of the plug 1221, as shown in FIG. 12B. An opened position may be achieved when a user makes an upward quarter or half turn of the mixing tip 1230 to disengage the disc 1226. In other words, the plug 1221 is freely suspended within the tip portion 1231 after an upward quarter or half turn of the mixing tip 1230. Thus, when appropriate force is applied from the double-plunger assembly 1212 to the components in the barrels 1214L, 1214R, the disengaged plug 1221 is accordingly lifted away from the closed position to allow the component in each barrel to move toward the tip portion of the mixing tip 1230 where the components are mixed to form an admixture for dispensing. The syringe in the present embodiment can be resealed simply by screwing down the mixing tip 1230 again.

The size of the disc 1226 is at least the same size as the discharge end of the neck portion 1223, so as to cover the discharge end thereof to minimize or prevent the components in the barrels 1214L, 1214R from leaking or premature mixing with the other component.

Figure 13:
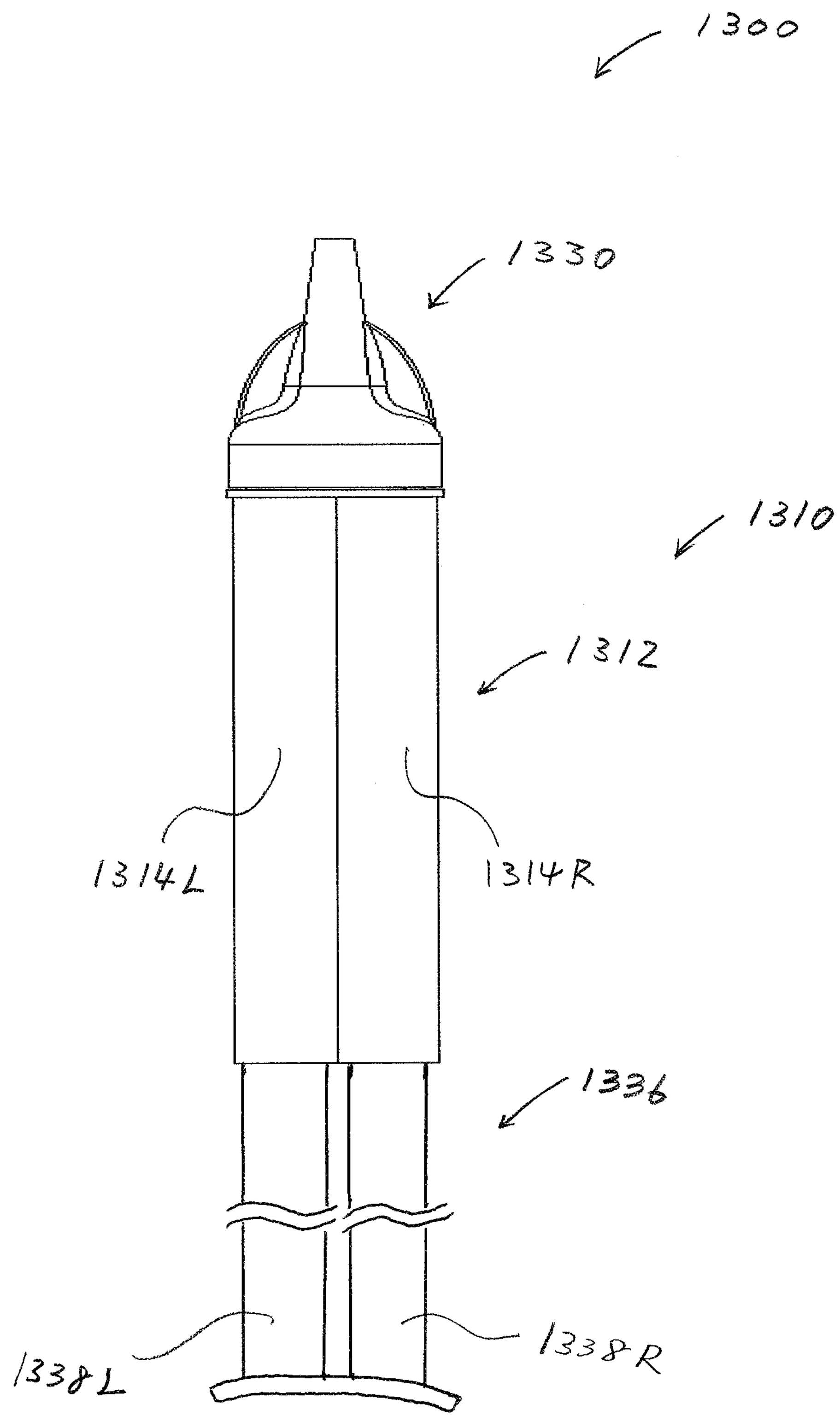
FIG. 13 is a perspective view of another double-barrel syringe including a rotatable mixing tip.
Figure 13A:
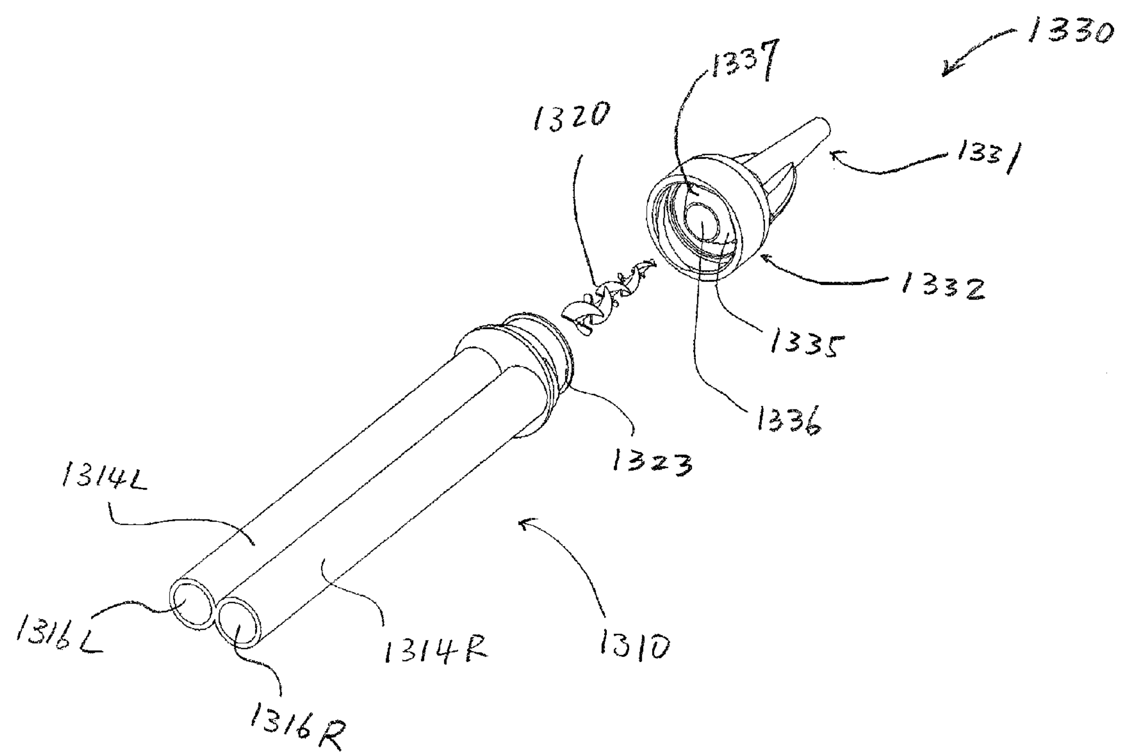
FIG. 13A is an exploded perspective view of the syringe in FIG. 13, including a mixing tip, a mixing element and a syringe barrel.

In some aspects, the rotatable mixing tip itself may serve as a plug which is also not integrated with the mixing element. As shown in FIGS. 13 and 13A, for example, the syringe 1300 may include a syringe barrel 1310, a mixing and switching assembly 1320 including a hemispheric channel blocker 1321 and a mixing element 1322, and a rotatable mixing tip 1330. Similar to other embodiments previously illustrated, the syringe barrel 1310 may include a double-barrel assembly 1312 that may have, for example, juxtaposed first and second generally cylindrical barrels 1314L, 1314R, respectively, which may have a common length and a generally cylindrical bore 1316L, 1316R, respectively. The syringe barrel 1310 may further include a double-plunger assembly 1336 that may have juxtaposed generally cylindrical first and second plungers 1338L, 1338R of a common length.

Figure 13B:
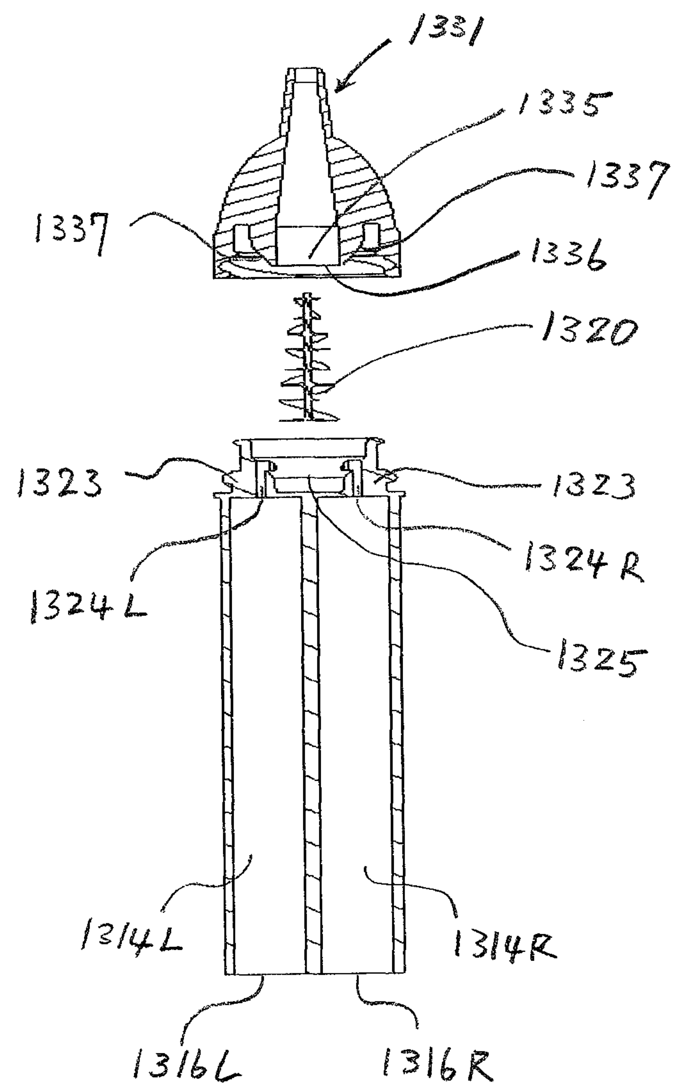
FIG. 13B is a partial cross-sectional perspective view of the syringe in FIG. 13A.

Referring to FIG. 13A and FIG. 13B, a pre-mixing neck portion 1323 may have juxtaposed first and second connecting channels 1324L, 1324R, respectively. Each connecting channel extends from an outlet of each cylindrical barrel 1314L, 1314R, respectively, to the discharge end of the neck portion 1323. The connecting channels 1324L and 1324R are compartmentalized by a separation unit 1325.

The mixing tip 1330 may include a tip portion 1331 and a thread portion 1332. The mixing element 1320 is closely received and wedged within the bore of the tapered tip portion 1331. The thread portion 1332 is adapted to attach to the pre-mixing neck portion 1323 by screwing onto portion of the outer surface thereof to control the position of the mixing tip 1330.

Still referring to FIGS. 13A and 13B, the hemispheric channel blocker 1321 may be, for example, integrated with the tip portion 1331 and located within the mixing tip 1330. More for example, the hemispheric channel blocker 1321 extends downwardly from lower tip portion 1331, and is located between the tip portion 1331 and the thread portion 1332, wherein the hemispheric channel blocker 1321, with a hollow interior, has an opening 1326 with full fluid communication with the bore of the tapered tip portion 1331, which receives and wedges the mixing element 1322. In other words, at least portion of the mixing element 1322 may be located within the hemispheric channel blocker 1321.

Figure 13C:
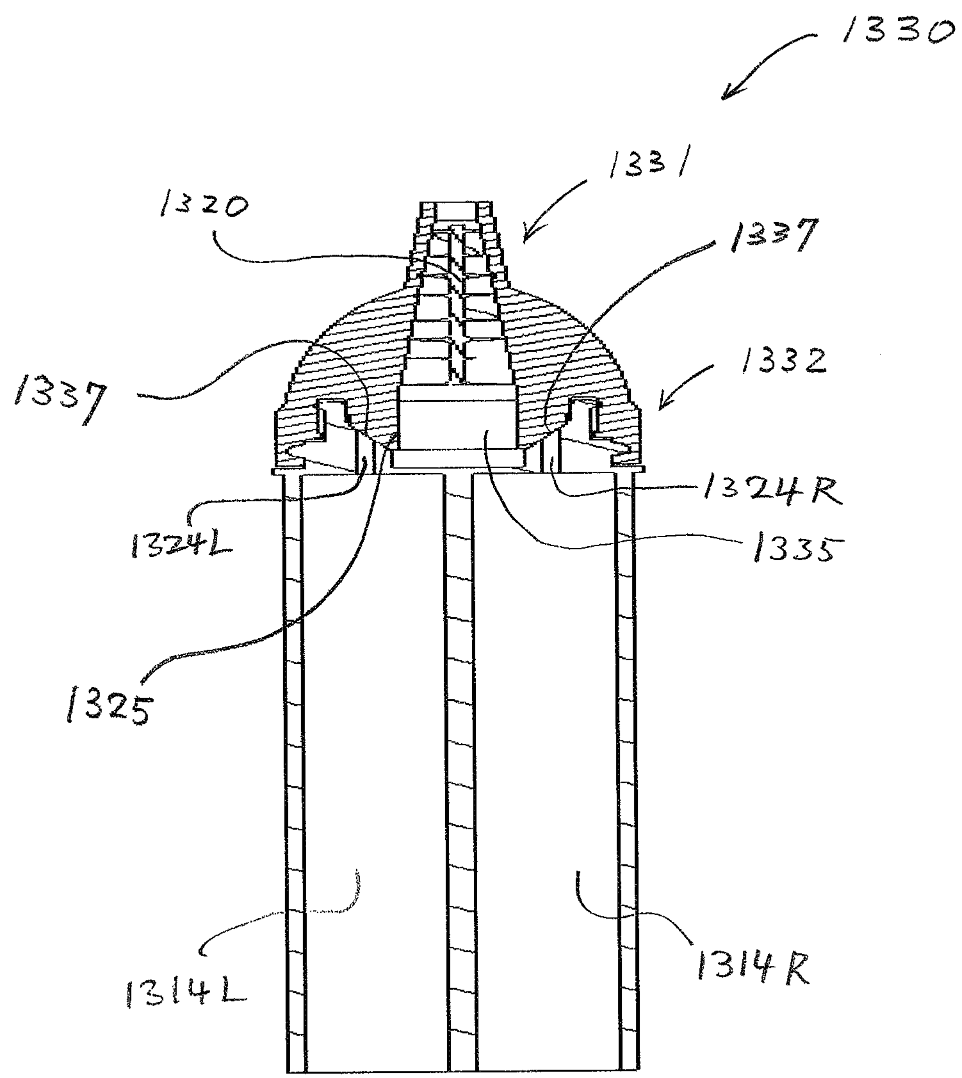
FIG. 13C is a partial cross-sectional perspective view of the syringe when the syringe is in its closed position.

The separation unit 1325 is arranged to receive the channel blocker 1321 wherein the size and shape of the separation unit 1325 is designed to tightly fit with an outer surface 1327 of the hemispheric channel blocker 1321, which is adapted to substantially block the connecting channel 1324L, 1324R, respectively. As can be seen in FIG. 13C, for example, when a user screws the mixing tip 1330 all the way down to close it, the outer surface 1327 of the hemispheric channel blocker 1321 is accordingly moved down to substantially block the connecting channels 1324L, 1324R, respectively, and a tight seal of each connecting channel is formed to prevent the components from premature mixing with each other.

An opened position of the syringe may be achieved when the user makes an upward quarter or half turn of the mixing tip 1330 to move the hemispheric outer surface 1327 away from the connecting channels 1324L, 1324R, respectively. Thus, when appropriate force is applied from the double-plunger assembly 1312 to the components in the barrels 1314L, 1314R, the component in each barrel is allowed to move toward the tip portion of the mixing tip 1330 where the components are mixed to form an admixture for dispensing. The syringe in the present embodiment can be resealed simply by screwing down the mixing tip 1330 again.

It is worth mentioning that since the size (e.g. diameter) of the connecting channels (1024L, 1024R, 1124L, 1124R, 1224L, 1224R, 1324L, 1324R) is relatively smaller than that of the barrels (1014L, 1014R, 1114L, 1114R, 1214L, 1214R, 1314L, 1314R), relatively higher pressure may be applied by the user to force the components from the barrels to the connecting channels. In other words, the flow rate decreases when the components move from the barrels to the connecting channels. Accordingly, the retention time of the components in the mixing element increases, and the mixing is thus enhanced.

In some aspects, the static mixing element may be formed integrally with the tip of a syringe. FIG. 9 illustrates an embodiment of a mixing and dispensing tip 900 that may include integral static mixing formations. The tip 900 may be formed from as a single component with multiple sections 902 that may form a full tip 900 when assembled. For example, the multiple sections 902 may be sectors of a cylinder, sectors of a cone, sections of prism, and/or any other appropriate components of a physical form that may be utilized as a tip. The tip 900 may include any number of sections 902 that may be effective in constructing a fully formed tip. In general, a greater number of sections may not necessarily improve the performance and/or usability of the tip and thus a low number, such as two or three sections, may be utilized to simplify design, construction and/or assembly. The sections may include hinges 906 between them. The hinges 906 may be, for example, living hinges such that they may be integrally constructed into the tip 900 and may not require any additional manufacture or assembly.

Figure 9A:
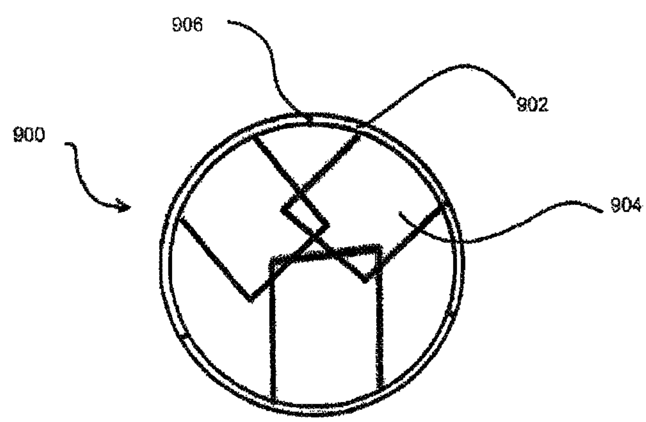
FIG. 9A is a axial view of an assembled mixing and dispensing tip with integral static mixing formations of FIG. 9.

The sections 902 may include on their inner surfaces multiple fins or baffles 904. The fins or baffles 904 may be angled, spaced and/or staggered in any appropriate configuration such as, for example, at an offset in each section such that when assembled, the fins or baffles 904 alternate from each section from one end of the tip to the other. The fins or baffles 904 may also be of an appropriate size such that they may provide an adequate mixing environment and may allow the composition to substantially pass through the tip 900 without significant obstruction to the flow. The fins or baffles may also overlap when the tip 900 is assembled and viewed from either end, as illustrated in FIG. 9A.

Figure 9C:
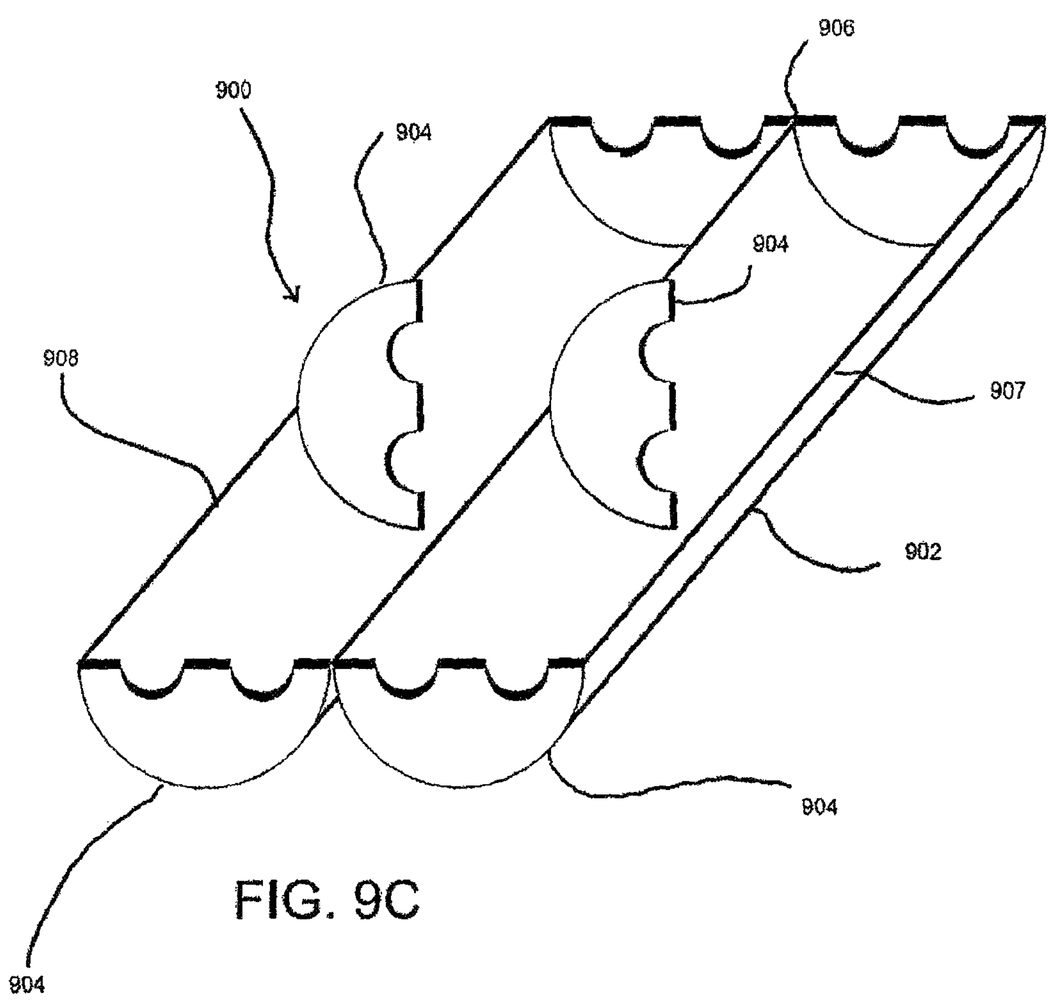
FIG. 9C is a perspective view of a mixing and dispensing tip with integral static mixing formations.
Figure 9D:
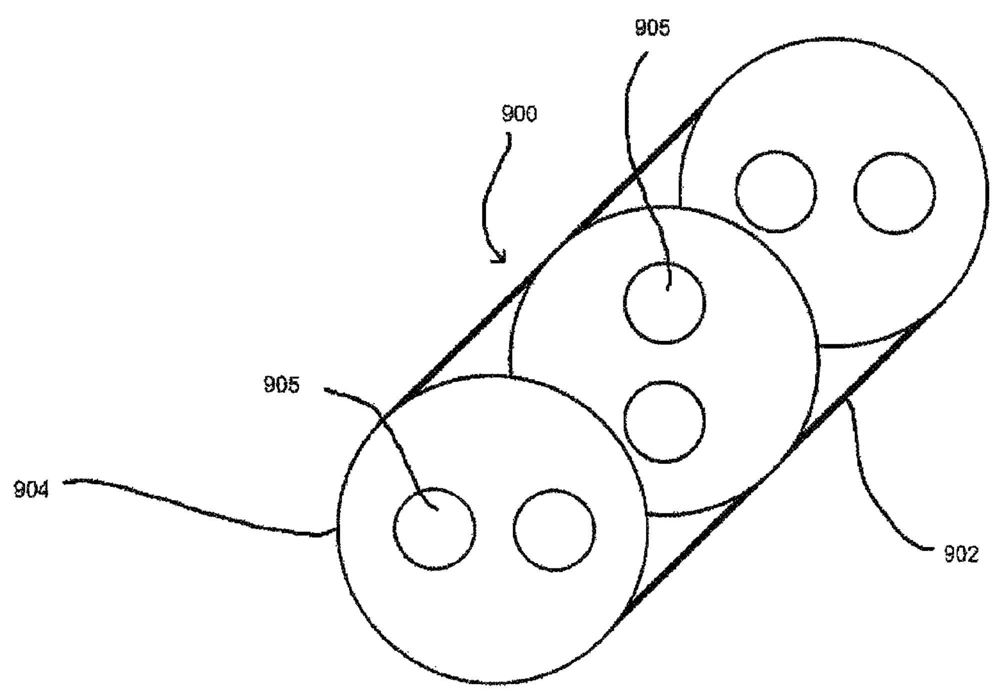
FIG. 9D is a partial see-through perspective view of an assembled mixing and dispensing tip with integral static mixing formations of FIG. 9C.

In other embodiments, the tip 900 may include a static mixing element where the fins or baffles 904 may form flow obstructions with offset flow channels. FIG. 9C illustrates an embodiment of a dispensing and mixing tip 900 that may include multiple sections 902. The multiple sections 902 may include disposed on their inner surface a series of fins or baffles 904 that, when the tip 900 is properly assembled, may substantially form flow obstructions. The fins or baffles 904 may, as shown in FIG. 9D, form portions of an internal structure that may substantially block flow. The flow obstructions may occur at regular or irregular intervals through the length of the tip 900. Each obstruction that may be formed by a particular set of fins or baffles 904 may also include a set of holes or flow channels 905 that may substantially allow passage of a flow therethrough. The holes or flow channels 905 may be formed in a regular pattern on each obstruction and may, in general, be situated around the central axis of the tip 900. The holes or flow channels 905 may further be offset from each other in each successive obstruction such that, when viewed from one end of tip 900, no straight-through flow path may be formed by the holes or flow channels 905. This configuration may allow the obstructions and the holes or flow channels 905 to form a static mixing element, as a multiphase flow entering from one end may be substantially split and recombined in multiple radial orientations about the center axis of the tip 900, and may be substantially mixed upon exiting from the outlet end.

The tip 900 may be assembled by rolling the sections 902 onto each other such that the free edges 907, 908 meet, utilizing the living hinges 906. The free edges 907, 908 may be joined by a variety of methods including, but not limited to, adhesives, welding, melting, fasteners, and/or any other appropriate method. Alternatively, the tip 900 may be housed within an external form 910, such as, for example, a cylinder, cone or other shape appropriate to the shape of the tip 900, such that the external form 910 may serve to hold the tip together, as shown in FIG. 9B.

In some embodiments, the tip 900 may be adapted form a dynamic mixing element. The tip 900 may be adapted to move within the external form 910 in, for example, a rotational manner, such that the fins or baffles 904 may serve as the effective moving parts of a dynamic mixing element.

The tip 900 may be manufactured by a variety of methods, including, but not limited to, injection molding, extrusion, casting, machining, and/or any other appropriate method, and may be fabricated as a unit from a suitable material, such as, for example, polymeric materials that may include polypropylene, polyethylene, polycarbonate, polyacrylic polymers, polystyrene and/or any other suitable material, as mentioned before.

Figure 10E:
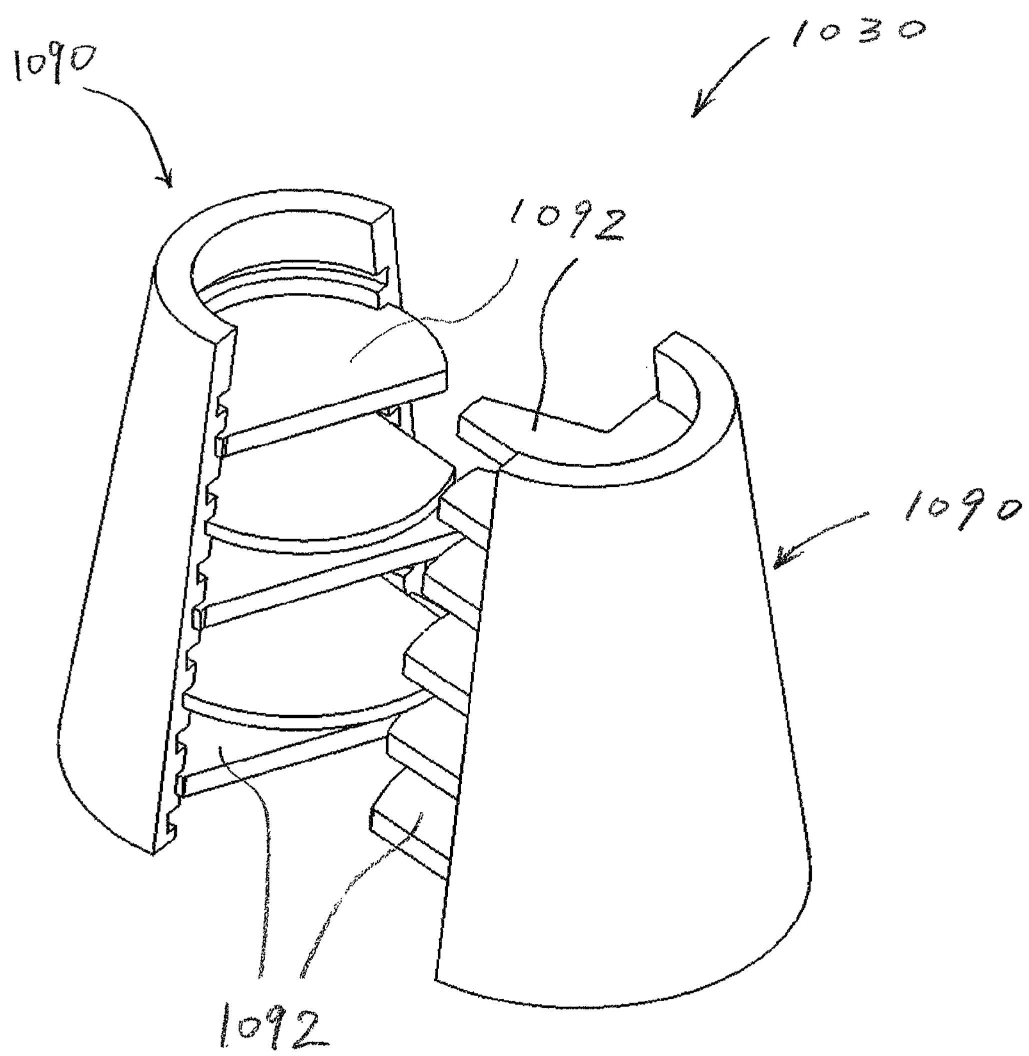
FIG. 10E is a perspective view of the rotatable head with integral static mixing formations.

In some embodiments, the mixing element may be formed integrally within the rotatable head 1030 as shown in FIG. 10E. The rotatable head 1030 may be formed from as a single component with multiple sections 1090 that may form a full tip portion of the rotatable head 1030 when assembled. In the present embodiment, two sections may be utilized to simplify design, construction and/or assembly. The sections 1090 may include on their inner surfaces multiple fins or baffles 1092. The fins or baffles 1092 may be angled, spaced and/or staggered in any appropriate configuration such as, for example, at an offset in each section such that when assembled, the fins or baffles 1092 alternate from each section from one end of the tip to the other. The fins or baffles 1092 may also be of an appropriate size such that they may provide an adequate mixing environment and may allow the composition to substantially pass through the tip portion of the rotatable head without significant obstruction to the flow. The fins or baffles 1092 may also overlap when the rotatable head 1030 is assembled and viewed from the top, as illustrated in FIG. 10E.

Figure 10F:
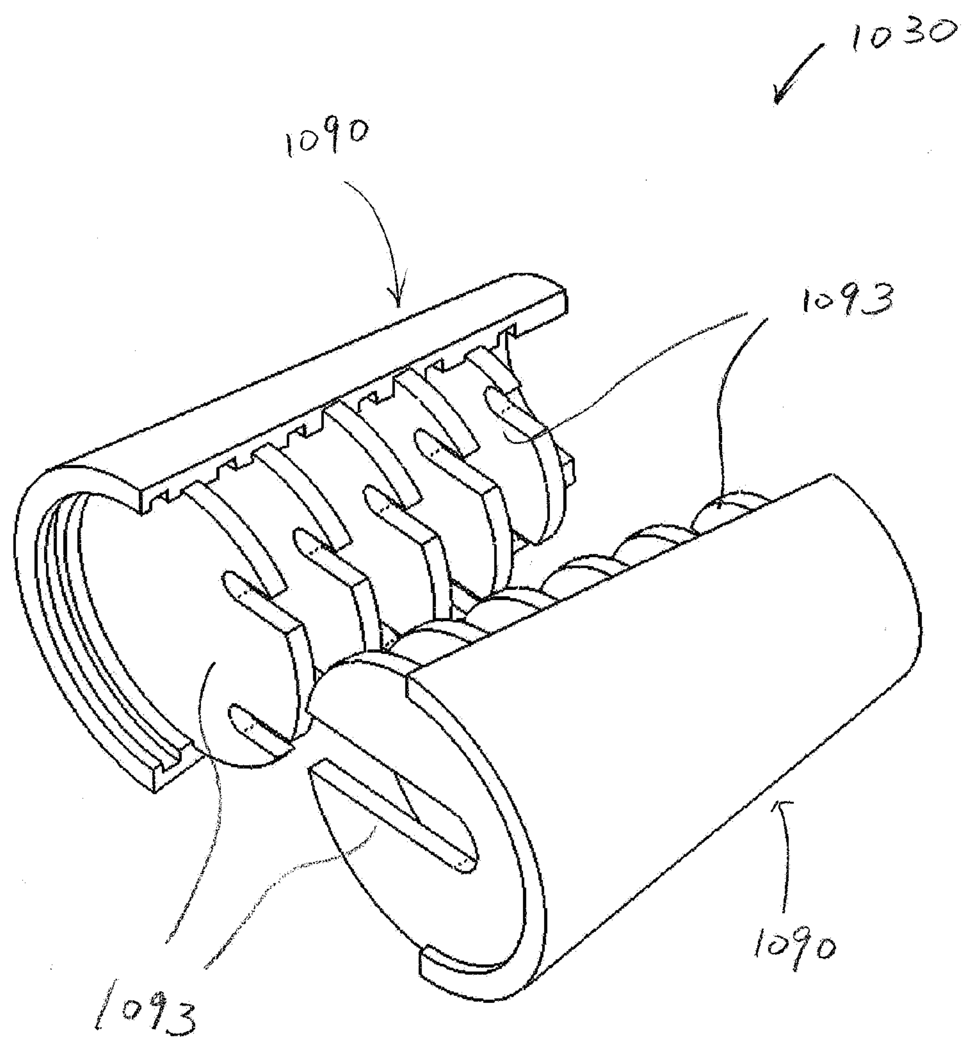
FIG. 10F is a perspective view of the rotatable head with integral static mixing formations of another embodiment.
Figure 10G:
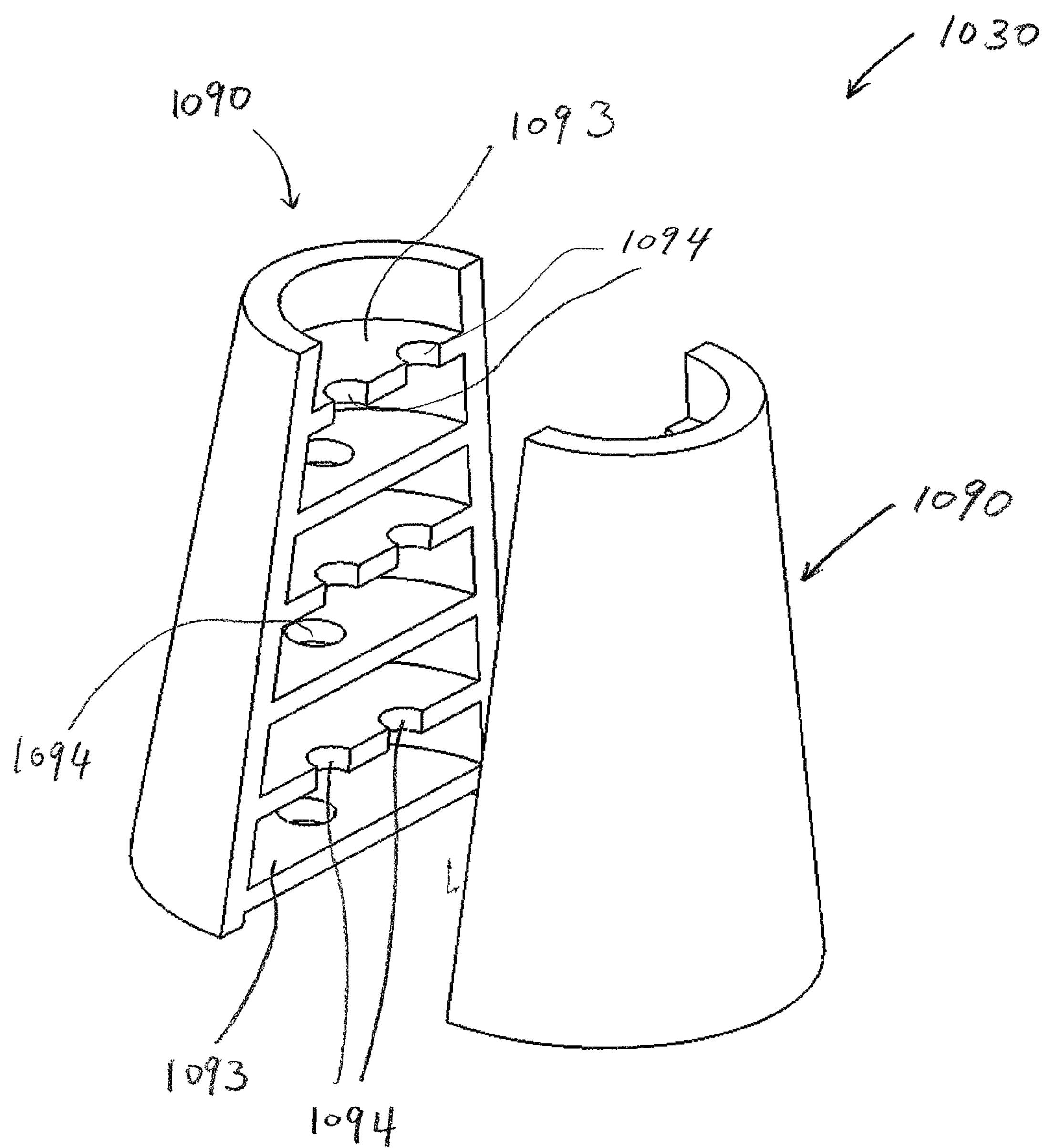
FIG. 10G is a perspective view of the rotatable head with integral static mixing formations forming flow channels.

In other embodiments, the tip portion of the rotatable head 1030 may include a mixing element where the fins or baffles 1093 may form flow obstructions with offset flow channels. As shown in FIG. 10F, the multiple sections 1090 may include a series of fins or baffles 1093 disposed on their inner surface, which may substantially form flow obstructions when the rotatable head 1030 is properly assembled. The fins or baffles 1093 may, as shown in FIG. 10H, form portions of an internal structure that may substantially block flow. The flow obstructions may occur at regular or irregular intervals through the length of the tip portion of the rotatable head 1030. In one embodiment, each obstruction that may be formed by a particular set of fins or baffles 1093 may also include a set of holes or flow channels 1094 that may substantially allow passage of a flow therethrough, as can be seen in FIG. 10G. The holes or flow channels 1094 may be formed in a regular or irregular pattern on each obstruction and may, in general, be situated about the central axis of the tip portion 1032 of the rotatable head 1030. The holes or flow channels 1094 may further be offset from each other in each successive obstruction such that, when viewed from the top of the rotatable head 1030, no straight-through flow path may be formed by the holes or flow channels 1094. This configuration may allow the obstructions and the holes or flow channels 1094 to form a mixing element, as a multiphase flow entering from one end may be substantially split and recombined in multiple radial orientations about the center axis of the rotatable head 1030, and may be substantially mixed upon exiting from the outlet end.

As noted above, the components may be mixed in various proportions such as 1:1, 1:2, 1:3, 1:4, 1:5 or so on, and thus the compartments or chambers of the syringe or container may be of the same or different sizes or diameters, as desired. Also, the number of compartments or chambers may vary from two to more than two.

While exemplified embodiments of the invention have been described and illustrated above, it should be understood that these are exemplary of the invention and are not to be considered as limiting. Accordingly, the invention is not to be considered as limited by the foregoing description, but is only limited by the scope of the claims appended hereto.

The invention claimed is:

1. A multi-chambered device for storing and dispensing the material components of an admixture, comprising:

a housing having at least two chambers, each of said chambers having an outlet and an inlet with full fluid communication between the inlet and the outlet;

a dispensing tip attached to the housing about the outlets of the chambers, said tip comprising a generally axial bore, an inlet and a discharge end;

at least one sealing system for substantially sealing the outlets of the chambers during storage, the at least one sealing system comprising at least one cap plug for substantially plugging the outlet of the chambers; and at least one seal breaking component configured to puncture or remove the sealing system when an appropriate force is applied thereto for effecting the unsealing of the outlets of the chambers, the at least one seal breaking component comprising a shaft, the at least one cap plug being coupled to the shaft, the shaft extending beyond the discharge end of the dispensing tip, such that it is accessible to a user without detaching the dispensing tip;

wherein at least a portion of said shaft is disposed within said bore.

2. The device of claim 1, wherein pulling the shaft removes the at least one cap plugs from the outlets of the chambers.

3. The device of claim 1, further comprising a unitary construction multi-plunger having juxtaposed plungers, the multiple plungers being connected to one another at a proximal end.

4. The device of claim 1 wherein said at least one dispensing tip further comprises a static mixing element or a dynamic mixing element, disposed within the bore for mixing at least two materials dispensed from the chambers.

5. The device of claim 4, wherein the static mixing element comprises a plurality of single turn screws, each screw rotatable in a direction opposite that of an adjacent screw and oriented at 90 degrees with respect thereto such that as multiple materials flow from one screw to the next screw the materials are split into two portions to effect mixing thereof.

6. The device of claim 1, wherein the at least one cap plug is attached to a static mixing element disposed within the bore.

7. The device of claim 1, wherein the accessible shaft extends from a static mixing element disposed within the bore.

8. The device of claim 1, wherein the chambers are at least partially filled at the outlet end with a substantially chemically inert material with respect to the contents of the chamber and the structure of the device.

9. The device of claim 1, further comprising a cap that substantially closes the outlet end of the dispensing and/or mixing tip.

10. A multi-chambered device for storing and dispensing material components of an admixture, comprising:

a housing having at a plurality of chambers, each of said plurality of chambers having an outlet and an inlet with full fluid communication between the inlet and the outlet;

a dispensing tip attached to the housing about the outlets of the chambers, said dispensing tip comprising a generally axial bore, an inlet proximate the outlets of the chambers, and an outlet;

at least one sealing system for substantially sealing the outlets of the chambers during storage, said sealing system comprising at least one cap plug for substantially plugging the outlet of each of the plurality of chambers and a shaft that is accessible through the dispensing tip outlet to a user, without detaching the dispensing tip, for effecting unsealing said outlets of said plurality of chambers, at least a portion of said shaft being disposed within said bore.

11. The device of claim 10, wherein pulling the shaft removes the at least one cap plug from the outlets of the chambers.

12. The device of claim 10, wherein the shaft is coupled with the at least one plug.

13. The device of claim 10, further comprising a multi-plunger having a plurality of plungers, each of said plurality of plungers carried by a respective one of said plurality of chambers, the plurality of plungers being connected to one another at a proximal end.

14. The device of claim 10, wherein said at least one dispensing tip further comprises a static mixing element disposed within the bore for mixing at least two materials dispensed from the chambers.

15. The device of claim 14, wherein the at least one cap plug is attached to a first end of the static mixing element.

16. The device of claim 15, wherein the shaft extends from a second end of the static mixing element.

17. The device of claim 10, wherein the chambers are at least partially filled at the outlet end with a substantially chemically inert material intermediate the at least one cap plug and contents of each chamber.

18. The device of claim 10, further comprising a cap that substantially closes the outlet end of the dispensing tip.

19. The device of claim 18, wherein said cap comprises a formation which couples with a formation on said shaft.

* * * * *